United States Patent
Hadcock

(10) Patent No.: US 6,699,832 B2
(45) Date of Patent: Mar. 2, 2004

(54) METHODS OF TREATING OBESITY USING A NEUROTENSIN RECEPTOR LIGAND

(75) Inventor: John R. Hadcock, East Lyme, CT (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 09/841,276

(22) Filed: Apr. 24, 2001

(65) Prior Publication Data

US 2001/0046956 A1 Nov. 29, 2001

Related U.S. Application Data

(60) Provisional application No. 60/199,951, filed on Apr. 27, 2000.

(51) Int. Cl.$^7$ .......................... A61K 31/00; A01N 37/18
(52) U.S. Cl. ................................. 514/1; 514/2
(58) Field of Search ............................ 514/1, 2, 12, 17, 514/18, 235.5, 183, 312; 530/350, 327, 330; 424/130.1; 435/7.1

(56) References Cited

U.S. PATENT DOCUMENTS

| | | |
|---|---|---|
| 4,110,321 A | 8/1978 | Folkers |
| 5,204,354 A | 4/1993 | Chakravarty et al. |
| 5,217,953 A | 6/1993 | Gozes et al. |
| 5,250,558 A | 10/1993 | Chakravarty et al. |
| 5,407,916 A | 4/1995 | Wise et al. |
| 5,523,455 A | 6/1996 | Labeeuw et al. ............ 558/418 |
| 5,585,497 A | 12/1996 | Labeeuw et al. ......... 548/374.1 |
| 6,008,050 A | 12/1999 | Bergsma et al. |
| 6,022,856 A | 2/2000 | Caput et al. |
| 6,274,720 B1 * | 8/2001 | Lal et al. ................. 536/23.51 |

FOREIGN PATENT DOCUMENTS

| | | | |
|---|---|---|---|
| EP | 0647629 | 7/1999 | ......... C07D/231/14 |
| WO | WO0031262 | 2/2000 | |

OTHER PUBLICATIONS

Singh et al. (Dec. 1997) "Effects of Microinjections of Cholecystokinin and Neurotensin into Lateral Hypothalamus and Ventral Mesencephalon on Intracrainal Self–Stimulation." Pharmacology Biochemistry and Behavior 58(4): 893–898.*

Williams et al. (Oct. 1991) "Reduced Hypothalamic Neurotensin Concentrations in the Genetically Obese Diabetic (ob/ob) Mouse: Possible Relationship to Obesity." Metabolism 40(10): 1112–1116.*

Cheah (Jun. 1996) "Current Management of Obesity." Singapore Med J. 37(3): 299–303.*

Boules et al. (May 19, 2000) "A novel neurotensin peptide analog given extracranially decreases food intake weight in rodents." Brain Research 865(1): 35–44.*

Stanley et al. (1983) "Neurotensin: Effects of Hypothalamic and Intravenous Injections on Eating and Drinking in Rats." Peptide 4(4): 493–500.*

Beaurepaire et al. (1988) "Anorectic Effect of Calcitonin, Neurotensin and Bombesin Infused in the Area of the Bostral Part of the Nucleus of the Tractus Solitarius in the Rat." Peptides 9(4): 729–733.*

Levine et al. (1983) "Effect of Centrally Administered Neurotensin of Multiple Feeding Paradigms." Pharmacology Biochemistry & Behavior 18: 19–23.*

Hawkins (1986) "Central Nervous System Neurotensin and Feeding." Physiology & Behavior 36(1): 1–8.*

Bray (1992) "Peptides affect the intake of specific nutrients and the sympathetic nervous system." Am. J. Clin. Nutr. 55: 265S–271S.*

Morley (1987) "Neuropeptide Regulation of Appetite and Weight." Endocrine Review 8(3): 252–287.*

Luttinger et al. (1982) "The effect of neurotensin on food consumption in the rat." European Journal of Pharmacology 81(3): 49 503.*

Bailey & Flatt (Jul. 22, 1986) "Anorectic Effect of Fenfluramine, Cholecystokinin and Neurotensin in genetically obese (ob/ob) mice." Comparative Biochemistry and Physiology 84(3): 451–454.*

Sandoval & Kulkosky (1992) "Effects of Peripheral Neurotensin on Behavior of the Rat." Pharmacology Biochemistry and Behavior 41(2): 385–390.*

Hong et al. (1997) Design, synthesis and pharmacological evaluation of active pyrrole based, nonpeptide analogues of neurotensin(8–13). J. Chem. Soc. (Perkin Trans. 1): 2997–3003.*

Boules et al. (May 18, 2000) "A novel neurotensin peptide analog given extracranially decreases food intake and weight in rodents." Brain Research 865(1): 35–44.*

Wilding et al. , *Increased neuropeptide–Y messenger ribonucleic acid (mRNA) and decreased neurotensin mRNA in the hypothalamus of the obese (ob/ob) mouser, Endocrinology*; vol. 132, No. 5; (1993).

Feldberg, R. S., et al., *Evidence for a neurotensin receptor in rat adipose tissue; Experimental Biology 96 Part II;* Apr. 14–17, 1996, XP001017940, Washington, D.C., USA.

B. Kinkead, et al. *Does Neurotensin Mediate the Effects of Antipsychotic Drugs? Society of Biological Psychiatry.* 1999. vol. 46. pp. 340–351.

W.H. Rostene, et al. *Quantitative Autoradiographic Localization of Neurotensin Binding Sites in Lean and Obese Zucker Rats. Horm. Metabol.* 1985. Res. 17. pp. 692–693.

I. Dubuc, et al. *Identification of the Receptor Subtype Involved in the Analgesic Effect of Neurotensin. Journal of Neuroscience.* 1999. vol 19:1. pp. 503–610.

A.B.R. Thomson, et al. *[1] Inhibition of Lipid Absorption as an Approach to the Treatment of Obesity. Methods in Enzymology.* 1997. vol. 286. pp. 3–44.

J.P. Vincent, et al. *Neurotensin and Neurotensin Receptors. TIPS.* Jul. 1999. vol. 20. pp. 302–309.

* cited by examiner

*Primary Examiner*—Elizabeth Kemmerer
*Assistant Examiner*—Christopher James Nichols
(74) *Attorney, Agent, or Firm*—Peter C. Richardson; Gregg C. Benson; Robert M. Kennedy

(57) ABSTRACT

The present invention relates to methods of treating obesity, diabetes, sexual dysfunction, atherosclerosis, insulin resistance, impaired glucose tolerance, hypercholesterolemia or hypertrigylceridemia using a neurotensin receptor ligand. The present invention also relates to pharmaceutical compositions and kits that comprise a neurotensin receptor ligand.

1 Claim, No Drawings

METHODS OF TREATING OBESITY USING A NEUROTENSIN RECEPTOR LIGAND

CROSS-REFERENCE TO RELATED INVENTION

This application claims priority of U.S. provisional application No. 60/199,951, filed Apr. 27, 2000.

FIELD OF THE INVENTION

The present invention relates to methods of treating obesity, diabetes, sexual dysfunction (including erectile dysfunction), atherosclerosis, insulin resistance, impaired glucose tolerance, hypercholesterolemia, or hypertrigylceridemia using a compound that is a neurotensin receptor ligand. The present invention also relates to compositions and kits that comprise a neurotensin receptor ligand.

BACKGROUND OF THE INVENTION

Obesity is a devastating disease. In addition to harming physical health, obesity can wreak havoc on mental health because obesity affects self-esteem, which ultimately can affect a person's ability to interact socially with others. Unfortunately, obesity is not well understood, and societal stereotypes and presumptions regarding obesity only tend to exacerbate the psychological effects of the disease. Because of the impact of obesity on individuals and society, much effort has been expended to find ways to treat obesity, but little success has been achieved in the long-term treatment and/or prevention of obesity.

Neurotensin is a thirteen amino acid peptide that appears to have functions as a neurotransmitter and neuromodulator in the nervous system and as a local hormone in the periphery. Specifically, neurotensin is a neuromodulator of dopamine transmission and of anterior pituitary hormone secretion, and exerts potent hypothermic and analgesic effects in the brain. In the periphery, neurotensin is a paracrine and endocrine modulator of the digestive tract and acts as a growth factor on a variety of cells.

So far, three types of neurotensin receptors have been identified: neurotensin-1 receptors, neurotensin-2 receptors, and neurotensisn-3 receptors. (The neurotensin-3 receptor is also called sortlin or gp95.) The neurotensin-1 and neurotensin-2 receptors are G protein coupled receptors; the neurotensin-3 receptor is not a G protein coupled receptor.

SUMMARY OF THE INVENTION

The present invention provides methods of treating obesity, the methods comprising the step of administering to an obese patient or a patient at risk of becoming obese a therapeutically effective amount of a compound that is a neurotensin receptor ligand.

In a preferred embodiment of the methods, the neurotensin receptor ligand is a neurotensin-1 receptor ligand.

In another preferred embodiment of the methods, the neurotensin receptor ligand is a neurotensin-2 receptor ligand.

In another preferred embodiment of the methods, the neurotensin receptor ligand is a neurotensin-3 receptor ligand.

In another preferred embodiment of the methods, the ligand is an agonist.

In another preferred embodiment of the methods, the ligand is an antagonist.

In another preferred embodiment of the methods, the neurotensin receptor ligand is a neurotensin-1 receptor agonist.

Also provided are methods of treating obesity, the methods comprising the step of administering to an obese patient or a patient at risk of becoming obese a therapeutically effective amount of a compound that is a selective neurotensin-1 receptor agonist.

Also provided are pharmaceutical compositions comprising:
a) a compound that is a neurotensin receptor ligand; and
b) a second compound useful for the treatment of obesity, diabetes, sexual dysfunction, atherosclerosis, insulin resistance, impaired glucose tolerance, hypercholesterolemia or hypertrigylceridemia.

In a preferred embodiment of the compositions, the neurotensin receptor ligand is a neurotensin-1 receptor agonist.

In another preferred embodiment of the method, the second compound is a $\beta_3$-adrenergic receptor agonist, a cholecystokinin-A agonist, a monoamine reuptake inhibitor, a sympathomimetic agent, a serotoninergic agent, a dopamine agonist, a melanocyte-stimulating hormone receptor agonist or mimetic, a melanocyte-stimulating hormone receptor analog, a cannabinoid receptor antagonist, a melanin concentrating hormone antagonist, leptin, a leptin analog, a leptin receptor agonist, a galanin antagonist, a bombesin agonist, a neuropeptide-Y antagonist, a thyromimetic agent, dehydroeplandrosterone or an analog thereof, a glucocorticoid receptor agonist or antagonist, an orexin receptor antagonist, a urocortin binding protein antagonist, a glucagon-like peptide-1 receptor agonist, or a ciliary neurotrophic factor.

Also provided are kits that comprises:
a) a first pharmaceutical composition comprising a compound that is a neurotensin receptor ligand;
b) a second pharmaceutical composition comprising a compound that is useful for the treatment of obesity, diabetes, sexual dysfunction, atherosclerosis, insulin resistance, impaired glucose tolerance, hypercholesterolemia or hypertrigylceridemia; and
c) a container for the first and second compositions.

In a preferred embodiment of the kits, the neurotensin receptor ligand is a neurotensin-1 receptor agonist.

In another preferred embodiment of the kits, the second pharmaceutical composition comprises a compound that is a $\beta_3$-adrenergic receptor agonist, a cholecystokinin-A agonist, a monoamine reuptake inhibitor, a sympathomimetic agent, a serotoninergic agent, a dopamine agonist, a melanocyte-stimulating hormone receptor agonist or mimetic, a melanocyte-stimulating hormone receptor analog, a cannabinoid receptor antagonist, a melanin concentrating hormone antagonist, leptin, a leptin analog, a leptin receptor agonist, a galanin antagonist, a bombesin agonist, a neuropeptide-Y antagonist, a thyromimetic agent, dehydroepiandrosterone or an analog thereof, a glucocorticoid receptor agonist or antagonist, an orexin receptor antagonist, a urocortin binding protein antagonist, a glucagon-like peptide-1 receptor agonist, or a ciliary neurotrophic factor.

Also provided are methods of treating diabetes, sexual dysfunction, atherosclerosis, insulin resistance, impaired glucose tolerance, hypercholesterolemia or hypertrigylceridemia, the methods comprising the step of administering to a patient having or at risk of having, diabetes, sexual dysfunction, atherosclerosis, insulin resistance, impaired glucose tolerance, hypercholesterolemia or hypertrigylceridemia a therapeutically effective amount of a neurotensin receptor ligand.

In a preferred embodiment of the method, the neurotensin receptor ligand is a neurotension-1 receptor ligand.

DETAILED DESCRIPTION OF THE INVENTION

The present invention relates to methods of treating obesity, diabetes, sexual dysfunction (including erectile dysfunction), atherosclerosis, insulin resistance, impaired glucose tolerance, hypercholesterolemia or hypertrigylceridemia using a compound that is a neurotensin receptor ligand. In addition, the present invention provides pharmaceutical compositions and kits comprising a neurotensin receptor ligand.

In accordance with the present invention, obesity, diabetes, sexual dysfunction (including erectile dysfunction), atherosclerosis, insulin resistance, impaired glucose tolerance, hypercholesterolemia or hypertrigylceridemia can be treated by administering to an obese patient or a patent at risk of becoming obese or a patent having or at risk of having, diabetes, sexual dysfunction (including erectile dysfunction), atherosclerosis, insulin resistance, impaired glucose tolerance, hypercholesterolemia, or hypertrigylceridemia a therapeutically effective amount of a neurotensin receptor ligand. In a preferred embodiment of the invention, the neurotensin receptor ligand is a neurotensin-1 receptor ligand. In a more preferred embodiment of the invention, the neurotensin receptor ligand is a selective neurotensin-1 receptor agonist.

The term "therapeutically effective amount" means an amount of a compound or combination of compounds that treats a disease; ameliorates, attenuates, or eliminates one or more symptoms of a particular disease; or prevents or delays the onset of one of more symptoms of a disease.

The term "patient" means animals, such as dogs, cats, cows, horses, sheep, geese, and humans. Particularly preferred patients are mammals, including humans of both sexes.

The term "pharmaceutically acceptable" means that the substance or composition must be compatible with the other ingredients of a formulation, and not deleterious to the patient.

The terms "treating", "treat" or "treatment" include preventative (e.g., prophylactic) and palliative treatment.

The phrase "neurotensin receptor ligand" means a compound that binds to a neurotensin receptor, or a stereoisomer of the compound, a pharmaceutically acceptable salt of the compound or stereoisomer, a prodrug of the compound or stereoisomer, or a pharmaceutically acceptable salt of the prodrug. It is also contemplated that any additional pharmaceutically active compound used in combination with a neurotensin receptor ligand can be a stereoisomer of the additional active compound, a salt of the additional active compound or stereoisomer thereof, a prodrug of the additional compound or stereoisomer thereof, or a salt of the prodrug.

The phrase "neurotensin receptor agonist" means a neurotensin receptor ligand that activates a neurotensin receptor.

The phrase "neurotensin receptor antagonist" means a neurotensin receptor ligand that blocks activation of a neurotensin receptor.

The term "selective" means that a ligand binds with greater affinity to a particular receptor when compared with the binding affinity of the ligand to another receptor. Preferably, the binding affinity of the ligand for the first receptor is about 50% or greater than the binding affinity for the second receptor. More preferably, the binding affinity of the ligand to the first receptor is about 75% or greater than the binding affinity to the second receptor. Most preferably, the binding affinity of the ligand to the first receptor is about 90% or greater than the binding affinity to the second receptor. In a preferred embodiment of the invention, the ligand exhibits a greater binding affinity to one of the three neurotensin receptors. Particularly preferred ligands are those that bind with greater affinity to the neurotensin-1 receptors when compared with binding to the neurotesin-2 or neurotensin-3 receptors. It is contemplated that preferred compounds bind neurotensin receptors with micromolar or greater affinity. More preferred compounds bind neurotensin receptors with nanomolar or greater affinity. Preferred neurotensin receptor ligands of the present invention include compounds that are selective agonists of the neurotensin-1 receptor.

Neurotensin receptor ligands can be identified, for example, by screening a compound library. Methods of identifying agonists and antagonists of receptors are well known to those skilled in the art. Specific procedures that can be used to identify neurotensin receptor ligands are presented below.

Examples of known neurotensin receptor ligands include hormones such as neurotensin (also called NT(1–13)) and neuromedin N, non-peptide agonists such as those disclosed in U.S. Pat. No. 5,407,916, non-peptide antagonists such as 2-([1-{7-chloro-4-quinolinyl}-5-{2,6-dimethoxyphenyl}pyrazol-3yl]carboxylamino)tricyclo (3.3.1.1.[3.7) decan-2-carboxylic acid (SR48692), which is a selective neurotensin-1 receptor antagonist, and 2-(5,6-dimethylaminopropyl)-1-[4-{N-(3-dimethylaminopropyl)-N-methylcarbamoyl}-2-isopropylphenyl]-1H-pyrazole-3-carbonyl)aminoadamantane-2-carboxylic acid (SR142948A), which is a non-selective antagonist that binds with equal affinity at neurotensin-1 and neurotensin-2 receptors. Another compound that is a neurotensin binding ligand is levocabastine. In addition, U.S. Pat. Nos. 5,250,558 and 5,204,354 disclose neurotensin receptor antagonists, and U.S. Pat. No. 5,407,916 discloses peptidic neurotensin agonists. An example of a selective neurotensin-1 receptor agonist is native neurotensin [NT(1–13)], which has a $K_d$ of about 0.3 nM at the neurotensin-1 receptor and about 2–6 nM at the neurotensin-2 receptor. Another example of a selective neurotensin-1 receptor agonist is Trp11 NT(1–13), which shows a binding affinity of about 1 nM at the neurotensin-1 receptor and about 27 nM at the neurotensin-2 receptor. Trp11 NT(1–13) is NT(1–13) in which amino acid 11 is tryptophan.

The amino acid sequences and nucleotide sequences that encode each of the three human neurotensin receptors are known to those skilled in the art and can be found in GenBank under accession numbers NM_002531, Y10148, and NM_002569.

A neurotensin receptor ligand is administered to a patient in a therapeutically effective amount. A neurotensin receptor ligand can be administered alone or as part of a pharmaceutically acceptable composition. In addition, a compound or composition can be administered all at once, as for example, by a bolus injection, multiple times, such as by a series of tablets, or delivered substantially uniformly over a period of time, as for example, using transdermal delivery. It is also noted that the dose of the compound can be varied over time. A neurotensin receptor ligand can be administered using an immediate release formulation, a controlled release formulation, or combinations thereof. The term "controlled release" includes sustained release, delayed release, and combinations thereof.

In addition, a neurotensin receptor ligand can be administered alone, in combination with other neurotensin receptor ligands, or with other pharmaceutically active compounds. The other pharmaceutically active compounds can be intended to treat the same disease as the neurotensin receptor ligand or a different disease. If the patient is to receive or is receiving multiple pharmaceutically active compounds, the compounds can be administered simultaneously or sequentially in any order. For example, in the case of tablets, the active compounds may be found in one tablet or in separate tablets, which can be administered at once or sequentially in any order. In addition, it should be recognized that the compositions can be different forms. For example, one or more compounds may be delivered via a tablet, while another is administered via injection or orally as a syrup. All combinations, delivery methods and administration sequences are contemplated.

Since one aspect of the present invention contemplates the treatment of the diseases referenced with a combination of pharmaceutically active agents that may be administered separately, the invention further relates to combining separate pharmaceutical compositions in kit form. For example, a kit may comprise two separate pharmaceutical compositions comprising: 1) a neurotensin receptor ligand; and 2) a second pharmaceutically active compound. The kit also comprises a container for the separate compositions, such as a divided bottle or a divided foil packet. Additional examples of containers include syringes, boxes, bags, and the like. Typically, a kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

An example of a kit is a blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process recesses are formed in the plastic foil. The recesses have the size and shape of the tablets or capsules to be packed. Next, the tablets or capsules are placed in the recesses and a sheet of relatively stiff material is sealed against the plastic foil at the face of the foil which is opposite from the direction in which the recesses were formed. As a result, the tablets or capsules are sealed in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide a memory aid on the kit, e.g., in the form of numbers next to the tablets or capsules whereby the numbers correspond with the days of the regimen that the tablets or capsules so specified should be ingested. Another example of such a memory aid is a calendar printed on the card, e.g., as follows "First Week, Monday, Tuesday, . . . etc. . . . Second Week, Monday, Tuesday," etc. Other variations of memory aids will be readily apparent. A "daily dose" can be a single tablet or capsule or several pills or capsules to be taken on a given day. Also, a daily dose of a neurotensin receptor ligand can consist of one tablet or capsule, while a daily dose of the second compound can consist of several tablets or capsules and vice versa. The memory aid should reflect this and assist in correct administration of the active agents.

In another embodiment of the present invention, a dispenser designed to dispense the daily doses one at a time in the order of their intended use is provided. Preferably, the dispenser is equipped with a memory aid, so as to further facilitate compliance with the dosage regimen. An example of such a memory aid is a mechanical counter, which indicates the number of daily doses that have been dispensed. Another example of such a memory aid is a battery-powered micro-chip memory coupled with a liquid crystal readout, or audible reminder signal which, for example, reads out the date that the last daily dose has been taken and/or reminds one when the next dose is to be taken.

A neurotensin receptor ligand and other pharmaceutically active compounds, if desired, can be administered to a patient either orally, rectally, parenterally, (for example, intravenously, intramuscularly, or subcutaneously) intracisternally, intravaginally, intraperitoneally, intravesically, locally (for example, powders, ointments or drops), or as a buccal or nasal spray.

Compositions suitable for parenteral injection may comprise physiologically acceptable sterile aqueous or nonaqueous solutions, dispersions, suspensions, or emulsions, or may comprise sterile powders for reconstitution into sterile injectable solutions or dispersions. Examples of suitable aqueous and nonaqueous carriers, diluents, solvents, or vehicles include water, ethanol, polyols (propylene glycol, polyethylene glycol, glycerol, and the like), suitable mixtures thereof, triglycerides, including vegetable oils such as olive oil, or injectable organic esters such as ethyl oleate. A preferred carrier is Miglyol®. Proper fluidity can be maintained, for example, by the use of a coating such as lecithin, by the maintenance of the required particle size in the case of dispersions, and/or by the use of surfactants.

These compositions may also contain adjuvants such as preserving, wetting, emulsifying, and/or dispersing agents. Prevention of microorganism contamination of the compositions can be accomplished by the addition of various antibacterial and antifungal agents, for example, parabens, chlorobutanol, phenol, sorbic acid, and the like. It may also be desirable to include isotonic agents, for example, sugars, sodium chloride, and the like. Prolonged absorption of injectable pharmaceutical compositions can be brought about by the use of agents capable of delaying absorption, for example, aluminum monostearate and/or gelatin.

Solid dosage forms for oral administration include capsules, tablets, powders, and granules. In such solid dosage forms, the active compound is admixed with at least one inert customary excipient (or carrier) such as sodium citrate or dicalcium phosphate or (a) fillers or extenders, as for example, starches, lactose, sucrose, mannitol, or silicic acid; (b) binders, as for example, carboxymethylcellulose, alginates, gelatin, polyvinylpyrrolidone, sucrose, or acacia; (c) humectants, as for example, glycerol; (d) disintegrating agents, as for example, agar-agar, calcium carbonate, potato or tapioca starch, alginic acid, certain complex silicates, or sodium carbonate; (e) solution retarders, as for example, paraffin; (f) absorption accelerators, as for example, quaternary ammonium compounds; (g) wetting agents, as for example, cetyl alcohol or glycerol monostearate; (h) adsorbents, as for example, kaolin or bentonite; and/or (i) lubricants, as for example, talc, calcium stearate, magnesium stearate, solid polyethylene glycols, sodium lauryl sulfate, or mixtures thereof. In the case of capsules and tablets, the dosage forms may also comprise buffering agents.

Solid compositions of a similar type may also be used as fillers in soft or hard filled gelatin capsules using such excipients as lactose or milk sugar, as well as high molecular weight polyethylene glycols, and the like.

Solid dosage forms such as tablets, dragees, capsules, and granules can be prepared with coatings or shells, such as enteric coatings and others well known in the art. They may also contain opacifying agents, and can also be of such composition that they release the active compound or compounds in a delayed manner. Examples of embedding compositions that can be used are polymeric substances and waxes. The active compounds can also be in microencapsulated form, if appropriate, with one or more of the above-mentioned excipients.

Liquid dosage forms for oral administration include pharmaceutically acceptable emulsions, solutions, suspensions, syrups, and elixirs. In addition to the active compounds, the liquid dosage form may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propylene glycol, 1,3-butylene glycol, dimethylformamide, oils, in particular, cottonseed oil, groundnut oil, corn germ oil, olive oil, castor oil, sesame seed oil, Miglyol®, glycerol, tetrahydrofurfuryl alcohol, polyethylene glycols, fatty acid esters of sorbitan, or mixtures of these substances, and the like.

Besides such inert diluents, the composition can also include adjuvants, such as wetting agents, emulsifying and suspending agents, sweetening, flavoring, and perfuming agents.

Suspensions, in addition to the active compound, may contain suspending agents, as for example, ethoxylated isostearyl alcohols, polyoxyethylene sorbitol or sorbitan esters, microcrystalline cellulose, aluminum metahydroxide, bentonite, agar-agar, or tragacanth, or mixtures of these substances, and the like.

Compositions for rectal or vaginal administration can be prepared by mixing a neurotensin receptor ligand and any additional compounds with suitable non-irritating excipients or carriers such as cocoa butter, polyethylene glycol or a suppository wax, which are solid at ordinary room temperature, but liquid at body temperature, and therefore, melt in the rectum or vaginal cavity and release the neurotensin receptor ligand.

Dosage forms for topical administration of a neurotensin receptor ligand include ointments, powders, sprays and inhalants. The compound(s) are admixed under sterile conditions with a physiologically acceptable carrier, and any preservatives, buffers, and/or propellants that may be required. Opthalmic formulations, eye ointments, powders, and solutions are also contemplated as being within the scope of this invention.

A neurotensin receptor ligand can be administered to a patient at dosage levels in the range of about 0.1 to about 7,000 mg per day. A preferred dosage range is about 1 to about 100 mg per day. The specific dosage and dosage range that can be used depends on a number of factors, including the requirements of the patient, the severity of the condition or disease being treated, and the pharmacological activity of the compound being administered. The determination of dosage ranges and optimal dosages for a particular patient is well within the ordinary skill of one in the art in view of this disclosure.

The following paragraphs describe exemplary formulations, dosages, etc., useful for non-human animals. The administration of a neurotensin receptor ligand can be effected orally or non-orally, for example by injection. An amount of a neurotensin receptor ligand is administered such that a therapeutically effective dose is received, generally a daily dose which, when administered orally to an animal is usually between 0.01 and 1000 mg/kg of body weight, preferably between 0.1 and 50 mg/kg of body weight. Conveniently, the compound or compounds can be carried in the drinking water so that a therapeutic dose of the compound or compounds is ingested with the daily water supply. The compound or compounds can be directly metered into drinking water, preferably in the form of a liquid, water-soluble concentrate (such as an aqueous solution of a water-soluble salt). Conveniently, the compound or compounds can also be added directly to the feed, as such, or in the form of an animal feed supplement, also referred to as a premix or concentrate. A premix or concentrate in a carrier is more commonly employed for the inclusion of the compound or compounds in the feed. Suitable carriers are liquid or solid, as desired, such as water, various meals such as alfalfa meal, soybean meal, cottonseed oil meal, linseed oil meal, corncob meal and corn meal, molasses, urea, bone meal, and mineral mixes such as are commonly employed in poultry feeds. A particularly effective carrier is the respective animal feed itself; that is, a small portion of such feed. The carrier facilitates uniform distribution of the compound or compounds in the finished feed with which the premix is blended. It is important that the compound or compounds be thoroughly blended into the premix and, subsequently, the feed. In this respect, the compound or compounds may be dispersed or dissolved in a suitable oily vehicle such as soybean oil, corn oil, cottonseed oil, and the like, or in a volatile organic solvent and then blended with the carrier. It will be appreciated that the proportions of compound or compounds in the concentrate are capable of wide variation since the amount of active compound or compounds in the finished feed may be adjusted by blending the appropriate proportion of premix with the feed to obtain a desired level of the compound or compounds.

High potency concentrates may be blended by the feed manufacturer with proteinaceous carrier such as soybean oil meal or other meals, as described above, to produce concentrated supplements that are suitable for direct feeding to animals. In such instances, the animals are permitted to consume the usual diet. Alternatively, such concentrated supplements may be added directly to the feed to produce a nutritionally balanced, finished feed containing a therapeutically effective level of a compound of the present invention. The mixtures are thoroughly blended by standard procedures, such as in a twin shell blender, to ensure homogeneity.

If the supplement is used as a top dressing for the feed, it likewise helps to ensure uniformity of distribution of the compound or compounds across the top of the dressed feed.

For parenteral administration in non-human animals, the compound or compounds may be prepared in the form of a paste or a pellet and administered as an implant, usually under the skin of the head or ear of the animal.

Paste formulations can be prepared by dispersing a compound or compounds in pharmaceutically acceptable oil such as peanut oil, sesame oil, corn oil or the like.

Pellets containing a therapeutically effective amount of a compound or compounds can be prepared by admixing the compound with a diluent such as carbowax, carnauba wax, and the like, and a lubricant, such as magnesium or calcium stearate, can be added to improve the pelleting process.

It is, of course, recognized that more than one pellet may be administered to an animal to achieve the desired dose level. Moreover, it has been found that implants may also be made periodically during the animal treatment period in order to maintain the proper active agent level in the animal's body.

The terms pharmaceutically acceptable salts or prodrugs includes the salts and prodrugs of compounds that are, within the scope of sound medical judgment, suitable for use with patients without undue toxicity, irritation, allergic response, and the like, commensurate with a reasonable benefit/risk ratio, and effective for their intended use, as well as the zwitterionic forms, where possible, of the compounds.

The term "salts" refers to inorganic and organic salts of compounds. These salts can be prepared in situ during the final isolation and purification of a compound, or by separately reacting a purified compound with a suitable organic or inorganic acid or base, as appropriate, and isolating the salt thus formed. Representative salts include the hydrobromide, hydrochloride, sulfate, bisulfate, nitrate, acetate, oxalate, palmitiate, stearate, laurate, borate, benzoate, lactate, phosphate, tosylate, besylate, esylate, citrate, maleate, fumarate, succinate, tartrate, naphthylate, mesylate, glucoheptonate, lactobionate, and laurylsulphonate salts, and the like. These may include cations based on the alkali and alkaline earth metals, such as sodium, lithium, potassium, calcium, magnesium, and the like, as well as non-toxic ammonium, quaternary ammonium, and amine cations including, but not limited to, ammonium, tetramethylammonium, tetraethylammonium, methylamine, dimethylamine, trimethylamine, triethylamine, ethylamine, and the like. See, for example, S. M. Berge, et al., "Pharmaceutical Salts," *J Pharm Sci*, 66:1–19 (1977).

The term "prodrug" means a compound that is transformed in vivo to yield a therapeutically active compound. The transformation may occur by various mechanisms, such as through hydrolysis in blood. A discussion of the use of prodrugs is provided by T. Higuchi and W. Stella, "Prodrugs as Novel Delivery Systems," Vol. 14 of the *A.C.S. Symposium Series*, and in *Bioreversible Carriers in Drug Design*, ed. Edward B. Roche, American Pharmaceutical Association and Pergamon Press, 1987.

For example, if a compound contains a carboxylic acid functional group, a prodrug can comprise an ester formed by the replacement of the hydrogen atom of the acid group with a group such as $(C_1-C_8)$alkyl, $(C_2-C_{12})$alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N-$(C_1-C_2)$alkylamino$(C_2-C_3)$alkyl (such as β-dimethylaminoethyl), carbamoyl-$(C_1-C_2)$alkyl, N,N-di$(C_1-C_2)$alkylcarbamoyl-$(C_1-C_2)$alkyl and piperidino-, pyrrolidino- or morpholino$(C_2-C_3)$alkyl.

Similarly, if a compound comprises an alcohol functional group, a prodrug can be formed by the replacement of the hydrogen atom of the alcohol group with a group such as $(C_1-C_6)$alkanoyloxymethyl, 1-$((C_1-C_6)$alkanoyloxy)ethyl, 1-methyl-1-$((C_1-C_6)$alkanoyloxymethyl, 1-$((C_1-C_6)$alkoxycarbonyloxymethyl, N-$(C_1-C_6)$alkoxycarbonylaminomethyl, succinoyl, $(C_1-C_6)$alkanoyl, α-amino$(C_1-C_4)$alkanoyl, arylacyl and α-aminoacyl, or α-aminoacyl-α-aminoacyl, where each α-aminoacyl group is independently selected from the naturally occurring L-amino acids, $P(O)(OH)_2$, $—P(O)(O(C_1-C_6)$alkyl$)_2$ or glycosyl (the radical resulting from the removal of a hydroxyl group of the hemiacetal form of a carbohydrate).

If a compound comprises an amine functional group, a prodrug can be formed by the replacement of a hydrogen atom in the amine group with a group such as R-carbonyl, RO-carbonyl, NRR'-carbonyl where R and R' are each independently $((C_1-C_{10})$alkyl, $(C_3-C_7)$cycloalkyl, benzyl, or R-carbonyl is a natural α-aminoacyl or natural α-aminoacyl-natural α-aminoacyl, —C(OH)C(O)OY wherein Y is H, $(C_1-C_6)$alkyl or benzyl, $—C(OY_0)Y_1$ wherein $Y_0$ is $(C_1-C_4)$ alkyl and $Y_1$ is $((C_1-C_6)$alkyl, carboxy$(C_1-C_6)$alkyl, amino$(C_1-C_4)$alkyl or mono-N- or di-N,N-$(C_1-C_6)$alkylaminoalkyl, $—C(Y_2)Y_3$ wherein $Y_2$ is H or methyl and $Y_3$ is mono-N- or di-N,N-$(C_1-C_6)$ alkylamino, morpholino, piperidin-1-yl or pyrrolidin-1-yl.

A neurotensin receptor ligand may contain asymmetric or chiral centers, and therefore, exist in different stereoisomeric forms. It is contemplated that all stereoisomeric forms as well as mixtures thereof, including racemic mixtures, form part of the present invention. In addition, the present invention contemplates all geometric and positional isomers. For example, if a compound contains a double bond, both the cis and trans forms, as well as mixtures, are contemplated.

Mixtures of isomers, including stereoisomers can be separated into their individual isomers on the basis of their physical chemical differences by methods well know to those skilled in the art, such as by chromatography and/or fractional crystallization. Enantiomers can be separated by converting the enantiomeric mixture into a diasteromeric mixture by reaction with an appropriate optically active compound (e.g., alcohol), separating the diastereomers and converting (e.g., hydrolyzing) the individual diastereomers to the corresponding pure enantiomers. Also, some of the compounds of this invention may be atropisomers (e.g., substituted biaryls) and are considered as part of this invention.

A neurotensin receptor ligand may exist in unsolvated as well as solvated forms with pharmaceutically acceptable solvents such as water, ethanol, and the like. The present invention contemplates and encompasses both the solvated and unsolvated forms.

It is also possible that a neurotensin receptor ligand may exist in different tautomeric forms. All tautomers of a neurotensin receptor ligand are contemplated.

Those skilled in the art will recognize that compound names contained herein may be based on a particular tautomer of a compound. While the name for only a particular tautomer may be used, it is intended that all tautomers are encompassed by the name of the particular tautomer, and all tautomers are considered part of the present invention.

It is also intended that the invention disclosed herein encompass compounds that are synthesized in vitro using laboratory techniques, such as those well known to synthetic chemists; or synthesized using in vivo techniques, such as through metabolism, fermentation, digestion, and the like. It is also contemplated that compounds may be synthesized using a combination of in vitro and in vivo techniques.

The present invention also includes isotopically labeled compounds, which are identical to the non-isotopically labeled compounds, but for the fact that one or more atoms are replaced by an atom having an atomic mass or mass number different from the atomic mass or mass number usually found most abundantly in nature. Examples of isotopes that can be incorporated into compounds identified by the present invention include isotopes of hydrogen, carbon, nitrogen, oxygen, phosphorous, fluorine and chlorine, such as $^2H$, $^3H$, $^{13}C$, $^{14}C$, $^{15}N$, $^{18}O$, $^{17}O$, $^{31}P$, $^{32}P$, $^{35}S$, $^{18}F$, $^{135}I$ and $^{36}Cl$, respectively. Neurotensin receptor ligands, prodrugs thereof, and pharmaceutically acceptable salts of said ligands or of said prodrugs which contain the aforementioned isotopes and/or other isotopes of other atoms are within the scope of this invention. Certain isotopically labeled compounds of the present invention, for example those into which radioactive isotopes such as $^3H$ and $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. Further, substitution with heavier isotopes such as deuterium, i.e., $^2H$, may afford certain therapeutic advantages resulting from greater metabolic stability, for example increased in vivo half-life or reduced dosage requirements and, hence, may be preferred in some circumstances. Isotopically labeled compounds can generally be prepared by substituting a readily available isotopically labeled reagent for a non-isotopically labeled reagent.

The present invention relates to the use of neurotensin receptor ligands to treat obesity, diabetes, sexual dysfunction, atherosclerosis, insulin resistance, impaired glucose tolerance, hypercholesterolemia, or hypertrigylceridemia.

In addition, a neurotensin receptor ligand, particularly neurotensin-2 receptor ligands, can be used to treat hyperthermia; hypothermia; gastrointestinal ulcers; substance abuse; depression; Alzheimer's disease; tardive dyskinesia; panic attack; gastrointestinal reflux disorder; irritable bowel syndrome; diarrhea; cholic; dyspepsia; pancreatitis; esophagitis; gastroparesis; neurological diseases such as schizophrenia, psychoses, anxiety, manic depression, delirium dementia, severe mental retardation, and dyskinesias such as Huntington's disease and Tourett's syndrome; fungal and viral infections, including HIV-1 and HIV-2 infections; pain (i.e., an analgesic); cancer (including gastrointesitinal tumors); anorexia; bulimia; asthma; Parkinson's disease; acute heart failure; hypotension; hypertension; urinary retention; osteoporosis; angina pectoris; myocardial infarction; allergies; inflammation; or benign prostatic hypertrophy.

The methods of treatment of the present invention can also include combination therapy where other pharmaceutically active compounds useful for the treatment of obesity or other diseases are used in combination with a neurotensin receptor ligand.

It is known that obese patients have higher incidences of certain diseases such as atherosclerosis, hypercholesterolemia, hypertrigylceridemia, hypertension, sexual dysfunction (including erectile dysfunction), insulin resistance, impaired glucose tolerance, diabetes, [particularly non-insulin dependent diabetes mellitus (NIDDM or Type 2 diabetes)] and the diseases associated with diabetes such as nephropathy, neuropathy, retinopathy, cardiomyopathy, cataracts, and polycystic ovary syndrome. These diseases can be treated indirectly by treating obesity using a neurotensin receptor ligand or directly by treating the specific disease itself using a neurotensin receptor ligand. These diseases can be treated in the absence of obesity using a neurotensin receptor ligand.

In one embodiment of the invention, an obese patient or a patient at risk of becoming obese can be administered a combination of: 1) a neurotensin receptor ligand; and 2) an additional compound useful to treat obesity, diabetes [including (NIDDM) and the conditions and/or diseases associated with diabetes, such as nephropathy, neuropathy, retinopathy, cardiomyopathy, cataracts, and polycystic ovary syndrome], atherosclerosis, hypercholesterolemia, hypertrigylceridemia, sexual dysfunction (including erectile dysfunction), insulin resistance, or impaired glucose tolerance, or combinations of compounds useful to treat these diseases.

Sexual dysfunction occurs in males and females and includes hypoactive sexual desire disorder, sexual anhedonia and dyspareunia. Hypoactive sexual desire disorder is a disorder in which sexual fantasies and desire for sexual activity are persistently or recurrently diminished or absent, causing marked distress or interpersonal difficulties. Symptoms and signs of hypoactive sexual desire disorder include the patient complaining of a lack of interest in sex, even in ordinarily erotic situations. The disorder is usually associated with infrequent sexual activity, often causing serious conflict between partners. Sexual anhedonia is decreased or absent pleasure in sexual activity. Sexual anhedonia is almost always classified under hypoactive sexual desire disorder, because loss of pleasure typically results in loss of desire. Dyspareunia is painful coitus or attempted coitus.

Erectile dysfunction is another example of a sexual dysfunction. Erectile dysfunction, like obesity, is another condition that can result in severe emotional distress. Persons suffering from erectile dysfunction are unable to develop and/or maintain an erection of the penis. Historically, erectile dysfunction has been viewed as having biological and psychological components, and more effort appeared to be exerted on treating the psychological components of the condition. Only recently with the introduction of Viagra® have persons having this condition been offered an oral medicinal treatment.

Diabetes is found more frequently in obese patients than non-obese patients. In spite of the early discovery of insulin and its subsequent widespread use in the treatment of diabetes, and the later discovery of and use of sulfonylureas, biguanides and thiazolidenediones, such as troglitazone, rosiglitazone or pioglitazone, as oral hypoglycemic agents, the treatment of diabetes remains less than satisfactory.

The use of insulin currently requires multiple daily doses, usually by self-injection. Determination of the proper dosage of insulin requires frequent estimations of the sugar in urine or blood. The administration of an excess dose of insulin causes hypoglycemia, with effects ranging from mild abnormalities in blood glucose to coma, or even death. Treatment of non-insulin dependent diabetes mellitus (Type 2 diabetes, NIDDM) usually consists of a combination of diet, exercise, oral hypoglycemic agents, e.g., thiazolidenediones, and, in more severe cases, insulin. However, the clinically available hypoglycemic agents can have side effects that limit their use, or an agent may not be effective with a particular patient. In the case of insulin dependent diabetes mellitus (Type 1), insulin is usually the primary course of therapy. Additional hypoglycemic agents that have fewer side effects or succeed where others fail are needed.

Atherosclerosis, a disease of the arteries, is recognized to be a leading cause of death in the United States and Western Europe. The pathological sequence leading to atherosclerosis and occlusive heart disease is well known. The earliest stage in this sequence is the formation of "fatty streaks" in the carotid, coronary and cerebral arteries and in the aorta. These lesions are yellow in color due to the presence of lipid deposits found principally within smooth-muscle cells and in macrophages of the intima layer of the arteries and aorta. Further, it is postulated that most of the cholesterol found within the fatty streaks, in turn, give rise to development of "fibrous plaques," which consist of accumulated intimal smooth muscle cells laden with lipid and are surrounded by extra-cellular lipid, collagen, elastin and proteoglycans. The cells plus matrix form a fibrous cap that covers a deeper deposit of cell debris and more extra-cellular lipid. The lipid is primarily free and esterified cholesterol. The fibrous plaque forms slowly, and is likely in time to become calcified and necrotic, advancing to a "complicated lesion," which accounts for arterial occlusion and tendency toward mural thrombosis and arterial muscle spasm that characterize advanced atherosclerosis.

Epidemiological evidence has firmly established hyperlipidemia as a primary risk factor in causing cardiovascular disease (CVD) due to atherosclerosis. In recent years, leaders of the medical profession have placed renewed emphasis on lowering plasma cholesterol levels, and low density lipoprotein cholesterol in particular, as an essential step in prevention of CVD. The upper limits of "normal" are now known to be significantly lower than heretofore appreciated. As a result, large segments of Western populations are now realized to be at particularly high risk. Such independent risk factors include glucose intolerance, left ventricular hypertrophy, hypertension, and being of the male sex. Cardiovascular disease is especially prevalent among diabetic subjects, at least in part because of the existence of multiple independent risk factors in this population. Successful treatment of hyperlipidemia in the general population, and in diabetic subjects in particular, is therefore of exceptional medical importance.

Hypertension (or high blood pressure) is a condition that occurs in the human population as a secondary symptom to various other disorders such as renal artery stenosis, pheochromocytoma or endocrine disorders. However, hypertension is also evidenced in many patients in whom the causative agent or disorder is unknown. While such "essential" hypertension is often associated with disorders such as obesity, diabetes and hypertriglyceridemia, the relationship between these disorders has not been elucidated. Additionally, many patients display the symptoms of high blood pressure in the complete absence of any other signs of disease or disorder.

It is known that hypertension can directly lead to heart failure, renal failure and stroke (brain hemorrhaging). These conditions are capable of causing death in a patient. Hypertension can also contribute to the development of atherosclerosis and coronary disease. These conditions gradually weaken a patient and can lead to death.

The exact cause of essential hypertension is unknown, though a number of factors are believed to contribute to the onset of the disease. Among such factors are stress, uncontrolled emotions, unregulated hormone release (the renin, angiotensin, aldosterone system), excessive salt and water due to kidney malfunction, wall thickening and hypertrophy of the vasculature resulting in constricted blood vessels and genetic factors.

The treatment of essential hypertension has been undertaken bearing the foregoing factors in mind. Thus, a broad range of beta-blockers, vasoconstrictors, angiotensin converting enzyme inhibitors and the like have been developed and marketed as antihypertensives. The treatment of hypertension utilizing these compounds has proven beneficial in the prevention of short-interval deaths such as heart failure, renal failure and brain hemorrhaging.

Hypertension has been associated with elevated blood insulin levels, a condition known as hyperinsulinemia. Insulin, a peptide hormone whose primary actions are to promote glucose utilization, protein synthesis and the formation and storage of neutral lipids, also acts to promote vascular cell growth and increase renal sodium retention, among other things. These latter functions can be accomplished without affecting glucose levels and are known causes of hypertension. Peripheral vasculature growth, for example, can cause constriction of peripheral capillaries while sodium retention increases blood volume. Thus, the lowering of insulin levels in hyperinsulinemics can prevent abnormal vascular growth and renal sodium retention caused by high insulin levels and thereby alleviate hypertension.

A neurotensin receptor ligand can be used in combination with one or more compounds that are useful to treat obesity. Examples of classes of compounds that can be used to treat obesity include the active compound(s) in appetite suppressants such as Adipex®, Bontril®, Desoxyn Gradumet®, Fastin®, Ionamin®, and Meridia®, and lipase inhibitors such as Xenical®.

Additional anti-obesity agents that can be used in combination with a neurotensin receptor ligand include a $\beta_3$-adrenergic receptor agonist, a cholecystokinin-A agonist, a monoamine reuptake inhibitor, a sympathomimetic agent, a serotoninergic agent, a dopamine agonist, a melanocyte-stimulating hormone receptor agonist or mimetic, a melanocyte-stimulating hormone receptor analog, a cannabinoid receptor antagonist, a melanin concentrating hormone antagonist, leptin, a leptin analog, a leptin receptor agonist, a galanin antagonist, a bombesin agonist, a neuropeptide-Y antagonist (including NPY-1 and NPY-5), a thyromimetic agent, dehydroepiandrosterone or an analog thereof, a glucocorticoid receptor agonist or antagonist, an orexin receptor antagonist, a urocortin binding protein antagonist, a glucagon-like peptide-1 receptor agonist, and a ciliary neurotrophic factor.

Especially preferred anti-obesity agents that can be used in combination with a neurotensin receptor ligand include compounds selected from the group consisting of sibutramine, fenfluramine, dexfenfluramine, bromocriptine, phentermine, orlistat, ephedrine, leptin, phenylpropanolamine, pseudoephedrine, {4-[2-(2-[6-aminopyridin-3-yl]-2(R)-hydroxyethylamino)ethoxy]phenyl}acetic acid, {4-[2-(2-[6-aminopyridin-3-yl]-2(R)-hydroxyethylamino)ethoxy]phenyl}benzoic acid, {4-[2-(2-[6-aminopyridin-3-yl]-2(R)-hydroxyethylamino)ethoxy]phenyl}propionic acid, and {4-[2-(2-[6-aminopyridin-3-yl]-2(R)-hydroxyethylamino)ethoxy]phenoxy}acetic acid.

Examples of thyromimetics that can be used in combination with a neurotensin receptor ligand include those disclosed in U.S. provisional patent application Nos. 60/178,968 and 60/177,987.

Examples of glucocorticoid receptor ligands that can be used in combination with a neurotensin receptor ligand include those disclosed in U.S. provisional patent application No. 60/132,130.

Examples of neuropeptide-Y antagonists that can be used in combination with a neurotensin receptor ligand include those disclosed in WO 98/23603, U.S. Pat. Nos. 5,900,415, 5,914,329, and U.S. provisional patent application No. 60/132,029 (NPY-5).

Examples of $\beta_3$-adrenergic receptor agonists that can be used in combination with a neurotensin receptor ligand include those disclosed in WO 96/35671.

Additional compounds that can be used to treat obesity and that can be used in combination with a neurotensin receptor ligand include the compounds disclosed in WO 98/46243.

Similarly, compounds that can be used to treat sexual dysfunction, and particularly erectile dysfunction, such as Viagra® can also be used in combination with a neurotensin receptor ligand. Other compounds that can be used to treat sexual dysfunction, particularly erectile dysfunction, and that can be used in combination with a neurotensin receptor ligand include apomorphine and IC351 (ICOS). A class of compounds that are useful to treat sexual dysfunction, particularly erectile dysfunction, are phophodiesterase V inhibitors. Examples of phosphodieserase V inhibitors can be found in U.S. Pat. No. 5,272,147.

In another aspect of the invention, a neurotensin receptor ligand can be administered in combination with a compound that is known to treat hypertension. Examples of classes of compounds that can be used to treat hypertension include calcium blockers, ACE inhibitors, diuretics, angiotensin II receptor blockers, β-blockers, and α-adrenergic blockers. In addition, combinations of compounds in the above-recited classes have been used to treat hypertension. Some examples of specific compounds that can be used in combination with neurotensin receptor ligands include quinapril; amlodipine, including the besylate salt; nifedipine; doxazosin, including the mesylate salt; and prazosin, including the hydrochloride salt.

In another aspect, a neurotensin receptor ligand can be used in combination with compounds useful for the treatment of diabetes, including impaired glucose tolerance, insulin resistance, insulin dependent diabetes mellitus (Type 1) and non-insulin dependent diabetes mellitus (NIDDM or Type 2). Also intended to be encompassed in the treatment of diabetes are the diabetic complications, such as neuropathy, nephropathy, retinopathy, cardiomyopathy or cataracts.

Representative agents that can be used to treat diabetes and which can be used in combination with a neurotensin receptor ligand include but are not limited to insulin and insulin analogs (e.g., LysPro insulin); GLP-1 (7–37) (insulinotropin) and GLP-1 (7–36)-$NH_2$; sulfonylureas and analogs: chlorpropamide, glibenclamide, tolbutamide, tolazamide, acetohexamide, glypizide, glimepiride, repaglinide, meglitinide; biguanides: metformin, phenformin, buformin; α2-antagonists and imidazolines: midaglizole, isaglidole, deriglidole, idazoxan, efaroxan, fluparoxan; other insulin secretagogues: linogliride, A-4166; glitazones: ciglitazone, pioglitazone, englitazone, troglitazone, darglitazone, BRL49653; fatty acid oxidation inhibitors: clomoxir, etomoxir; α-glucosidase inhibitors: acarbose, miglitol, emiglitate, voglibose, MDL-25,637, camiglibose, MDL-73,945; β-agonists: BRL 35135, BRL 37344, Ro 16-8714, ICI D7114, CL 316,243; phosphodiesterase inhibitors: L-386,398; lipid-lowering agents: benfluorex; antiobesity agents: fenfluramine and orlistat; vanadate and vanadium complexes (e.g., Naglivan®) and peroxovanadium complexes; amylin antagonists; glucagon antagonists; gluconeogenesis inhibitors; somatostatin agonists and antagonists; antilipolytic agents: nicotinic acid, acipimox, WAG 994; and glycogen phosphorylase inhibitors, such as those disclosed in WO 96/39385 and WO 96/39384. Also contemplated in combination with compounds of the present invention are pramlintide acetate (Symlin™) and nateglinide.

Preferred examples of glycogen phosphorylase inhibitors that can be used in the present invention in combination with a neurotensin receptor ligand include: 6H-thieno[2,3-b]pyrrole-5-carboxylic acid [(1S)-benzyl-3-((3R,4S)-dihydroxy-pyrrolidin-1-yl)-2R)-hydroxy-3-oxo-propyl]-amide;

2-bromo-6H-thieno[2,3-b]pyrrole-5-carboxylic acid [(1S)-benzyl-3-((3R,4S)-dihydroxy-pyrrolidin-1-yl)-(2R)-hydroxy-3-oxo-propyl]-amide;

2-methyl-6H-thieno[2,3-b]pyrrole-5-carboxylic acid [(1S)-benzyl-3-((3R,4S)-dihydroxy-pyrrolidin-1-yl)-(2R)-hydroxy-3-oxo-propyl]-amide;

(±)-2-methyl-6H-thieno[2,3-b]pyrrole-5-carboxylic acid [1-benzyl-2-((3R,4S)-dihydroxy-pyrrolidin-1-yl)-2-oxo-ethyl]-amide;

2-bromo-6H-thieno[2,3-b]pyrrole-5-carboxylic acid [(1S)-benzyl-2-((3R,4S)-dihydroxy-pyrrolidin-1-yl)-2-oxo-ethyl]-amide;

2-chloro-6H-thieno[2,3-b]pyrrole-5-carboxylic acid [(1S)-benzyl-3-((3R,4S)-dihydroxy-pyrrolidin-1-yl)-(2R)-hydroxy-3-oxo-propyl]-amide;

2-chloro-6H-thieno[2,3-b]pyrrole-5-carboxylic acid [(1S)-benzyl-2-((3R,4S)-dihydroxy-pyrrolidin-1-yl)-2-oxo-ethyl]-amide;

2,4-dichloro-6H-thieno[2,3-b]pyrrole-5-carboxylic acid [(1S)-benzyl-3-((3R,4S)-dihydroxy-pyrrolidin-1-yl)-(2R)-hydroxy-3-oxo-propyl]-amide;

(±)-4H-thieno[3,2-b]pyrrole-5-carboxylic acid [1-benzyl-2-((3R,4S)-dihydroxy-pyrrolidin-1-yl)-2-oxo-ethyl]-amide;

2-bromo-4H-thieno[3,2-b]pyrrole-5-carboxylic acid [(1S)-benzyl-3-((3R,4S)-dihydroxy-pyrrolidin-1-yl)-(2R)-hydroxy-3-oxo-propyl]-amide;

4H-thieno[3,2-b]pyrrole-5-carboxylic acid [(1S)-benzyl-3-((3R,4S)-dihydroxy-pyrrolidin-1-yl)-(2R)-hydroxy-3-oxo-propyl]-amide;

(±)-2-bromo-4H-furo[3,2-b]pyrrole-5-carboxylic acid [1-benzyl-2-((3R,4S)-dihydroxy-pyrrolidin-1-yl)-2-oxo-ethyl]-amide;

2-bromo-4H-furo[3,2-b]pyrrole-5-carboxylic acid [(1S)-benzyl-3-((3R,4S)-dihydroxy-pyrrolidin-1-yl)-(2R)-hydroxy-3-oxo-propyl]-amide;

6H-thieno[2,3-b]pyrrole-5-carboxylic acid [(1S)-benzyl-2-((3R,4S)-dihydroxy-pyrrolidin-1-yl)-2-oxo-ethyl]-amide;

2-bromo-4H-thieno[3,2-b]pyrrole-5-carboxylic acid [(1S)-benzyl-2-((3R,4S)-dihydroxy-pyrrolidin-1-yl)-2-oxo-ethyl]-amide;

2-methyl-4H-thieno[3,2-b]pyrrole-5-carboxylic acid [(1S)-benzyl-2-((3R,4S)-dihydroxy-pyrrolidin-1-yl)-2-oxo-ethyl]-amide;

2,4-dichloro-6H-thieno[2,3-b]pyrrole-5-carboxylic acid [(1S)-benzyl-2-((3R,4S)-dihydroxy-pyrrolidin-1-yl)-2-oxo-ethyl]-amide;

2-cyano-6H-thieno[2,3-b]pyrrole-5-carboxylic acid [(1S)-benzyl-2-(3-hydroxy-azetidin-1-yl)-2-oxo-ethyl]-amide;

2-chloro-6H-thieno[2,3-b]pyrrole-5-carboxylic acid [(1S)-benzyl-2-morpholin-4-yl-2-oxo-ethyl]-amide;

2-chloro-6H-thieno[2,3-b]pyrrole-5-carboxylic acid [(1S)-dimethylcarbamoyl-2-phenyl-ethyl]-amide;

2-chloro-6H-thieno[2,3-b]pyrrole-5-carboxylic acid [(1S)-benzyl-2-(1,1-dioxo-1-thiazolidin-3-yl)-2-oxo-ethyl]-amide;

1-{(2S)-[(2-chloro-6H-thieno[2,3-b]pyrrole-5-carbonyl)-amino]-3-phenyl-propionyl}-piperidine-4-carboxylic acid ethyl ester;

2-bromo-6H-thieno[2,3-b]pyrrole-5-carboxylic acid [(1S)-benzyl-2-(3-hydroxy-azetidin-1-yl)-2-oxo-ethyl]-amide;

2-methyl-4H-furo[3,2-b]pyrrole-5-carboxylic acid [(1S)-benzyl-2-((3R,4S)-dihydroxy-pyrrolidin-1-yl)-2-oxo-ethyl]-amide;

2-trimethylsilanylethynyl-6H-thieno[2,3-b]pyrrole-5-carboxylic acid [(1S)-benzyl-2-(3-hydroxy-azetidin-1-yl)-2-oxo-ethyl]-amide;

2-ethynyl-6H-thieno[2,3-b]pyrrole-5-carboxylic acid [(1S)-benzyl-2-(3-hydroxy-azetidin-1-yl)-2-oxo-ethyl]-amide;

2-fluoro-4H-thieno[3,2-b]pyrrole-5-carboxylic acid [(1S)-benzyl-2-((3R,4S)-dihydroxy-pyrrolidin-1-yl)-2-oxo-ethyl]-amide;

2-cyano-4H-furo[3,2-b]pyrrole-5-carboxylic acid [(1S)-benzyl-2-(3-hydroxy-azetidin-1-1-yl)-2-oxo-ethyl]-amide;

2-chloro-4H-furo[3,2-b]pyrrole-5-carboxylic acid [(1S)-benzyl-2-((3R,4S)-dihydroxy-pyrrolidin-1-yl)-2-oxo-ethyl]-amide;

2-chloro-4H-furo[3,2-b]pyrrole-5-carboxylic acid [(1S)-benzyl-3-((3R,4S)-dihydroxy-pyrrolidin-1-yl)-(2R)-hydroxy-3-oxo-propyl]-amide;

1-{(2S)-[(2-chloro-6H-thieno[2,3-b]pyrrole-5-carbonyl)-amino]-3-phenyl-propionyl}-piperidine-4-carboxylic acid;

3-chloro-4H-thieno[3,2-b]pyrrole-5-carboxylic acid [(1S)-benzyl-2-((3R,4S)-dihydroxy-pyrrolidin-1-yl)-2-oxo-ethyl]-amide;

3-chloro-4H-thieno[3,2-b]pyrrole-5-carboxylic acid [(1S)-benzyl-3-((3R,4S)-dihydroxy-pyrrolidin-1-yl)-(2R)-hydroxy-3-oxo-propyl]-amide;

3-bromo-4H-thieno[3,2-b]pyrrole-5-carboxylic acid [(1S)-benzyl-2-((3R,4S)-dihydroxy-pyrrolidin-1-yl)-2-oxo-ethyl]-amide;

3-bromo-4H-thieno[3,2-b]pyrrole-5-carboxylic acid [(1S)-benzyl-3-((3R,4S)-dihydroxy-pyrrolidin-1-yl)-(2R)-hydroxy-3-oxo-propyl]-amide;

2-chloro-4H-thieno[3,2-b]pyrrole-5-carboxylic acid [(1S)-benzyl-3-((3R,4S)-dihydroxy-pyrrolidin-1-yl)-(2R)-hydroxy-3-oxo-propyl]-amide;

2-chloro-4H-thieno[3 ,2-b]pyrrole-5-carboxylic acid [(1S)-benzyl-2-((3R,4S)-dihydroxy-pyrrolidin-1-yl)-2-oxo-ethyl]-amide;

3-methyl-4H-thieno[3,2-b]pyrrole-5-carboxylic acid [(1S)-benzyl-2-((3R,4S)-dihydroxy-pyrrolidin-1-yl)-2-oxo-ethyl]-amide;

3-methyl-4H-thieno[3,2-b]pyrrole-5-carboxylic acid [(1S)-benzyl-3-((3R,4S)-dihydroxy-pyrrolidin-1-yl)-(2R)-hydroxy-3-oxo-propyl]-amide;

2-cyano-4H-thieno[3,2-b]pyrrole-5-carboxylic acid [(1S)-benzyl-2-((3R,4S)-dihydroxy-pyrrolidin-1-yl)-2-oxo-ethyl]-amide;

2-cyano-4H-furo[3,2-b]pyrrole-5-carboxylic acid [(1S)-benzyl-3-((3R,4S)-dihydroxy-pyrrolidin-1-yl)-(2R)-hydroxy-3-oxo-propyl]-amide;

3-bromo-4H-furo[3,2-b]pyrrole-5-carboxylic acid [(1S)-benzyl-2-((3R,4S)-dihydroxy-pyrrolidin-1-yl)-2-oxo-ethyl]-amide;

3-bromo-4H-furo[3,2-b]pyrrole-5-carboxylic acid [(1S)-benzyl-3-((3R,4S)-dihydroxy-pyrrolidin-1-yl)-(2R)-hydroxy-3-oxo-propyl]-amide;

4H-1,7-dithia-4-aza-cyclopenta[a]pentalene-5-carboxylic acid [(1S)-benzyl-3-((3R,4S)-dihydroxy-pyrrolidin-1-yl)-(2R)-hydroxy-3-oxo-propyl]-amide;

4H-1,7-dithia-4-aza-cyclopenta[a]pentalene-5-carboxylic acid [(1S)-benzyl-2-((3R,4S)-dihydroxy-pyrrolidin-1-yl)-2-oxo-ethyl]-amide;

2-chloro-3-methyl-4H-thieno[3,2-b]pyrrole-5-carboxylic acid [(1S)-benzyl-2-((3R,4S)-dihydroxy-pyrrolidin-1-yl)-2-oxo-ethyl]-amide;

2-chloro-3-methyl-4H-thieno[3,2-b]pyrrole-5-carboxylic acid [(1S)-benzyl-3-((3R,4S)-dihydroxy-pyrrolidin-1-yl)-(2R)-hydroxy-3-oxo-propyl]-amide;

2-methylsulfanyl-4H-thieno[3,2-b]pyrrole-5-carboxylic acid [(1S)-benzyl-2-((3R,4S)-dihydroxy-pyrrolidin-1-yl)-2-oxo-ethyl]-amide;

2-Bromo-4H-thieno[3,2-b]pyrrole-5-carboxylic acid [(1S)-benzyl-2-(3-hydroxy-azetidin-1-yl)-2-oxo-ethyl]-amide;

2-Bromo-4H-thieno[3,2-b]pyrrole-5-carboxylic acid [(1S)-benzyl-2-(1,1-dioxo-1-thiazolidin-3-yl)-2-oxo-ethyl]-amide;

2-Bromo-4H-thieno[3,2-b]pyrrole-5-carboxylic acid [(1S)-benzyl-2-morpholin-4-yl-2-oxo-ethyl]-amide;

2-bromo-4H-thieno[3,2-b]pyrrole-5-carboxylic acid [(1S)-benzyl-2-((3S,4S)-dihydroxy-pyrrolidin-1-yl)-2-oxo-ethyl]-amide;

2-bromo-4H-thieno[3,2-b]pyrrole-5-carboxylic acid [(1S)-benzyl-2-((3R,4S)-dihydroxy-pyrrolidin-1-yl)-2-oxo-ethyl]-amide;

2-bromo-4H-thieno[3,2-b]pyrrole-5-carboxylic acid [(1S)-benzyl-2-(4-hydroxy-piperidin-1-yl)-2-oxo-ethyl]-amide; and the pharmaceutically acceptable salts and prodrugs thereof, and salts of the prodrugs.

Methods for making the above recited glycogen phosphorylase inhibitors can be found in U.S. provisional patent application No. 60/157,148, filed Sep. 30, 1999.

Commonly assigned PCT published applications WO 96/39384 and WO 96/39385 disclose additional glycogen phosphorylase inhibitors that can be used in combination with a neurotensin receptor ligand. Additional preferred glycogen phosphorylase inhibitors include:

5-chloro-1H-indole-2-carboxylic acid [(1S)-((R)-hydroxy-dimethylcarbamoyl-methyl)-2-phenyl-ethyl]-amide;

5,6-dichloro-1H-indole-2-carboxylic acid {(1S)-[(R)-hydroxy-(methoxy-methyl-carbamoyl)-methyl]-2-phenyl-ethyl}-amide;

5-chloro-1H-indole-2-carboxylic acid {(1S)-[(R)-hydroxy-(methoxy-methyl-carbamoyl)-methyl]-2-phenyl-ethyl}-amide;

5-chloro-1H-indole-2-carboxylic acid ((1S)-{(R)-hydroxy-[(2-hydroxy-ethyl)-methyl-carbamoyl]-methyl}-2-phenyl-ethyl)-amide;

5-chloro-1H-indole-2-carboxylic acid [(1S)-benzyl-3-((3R,4S)-dihydroxy-pyrrolidin-1yl)-(2R)-hydroxy-3-oxo-propyl]-amide;

5-chloro-1H-indole-2-carboxylic acid {(1S)-[(R)-hydroxy-(methyl-pyridin-2-yl-carbamoyl)-methyl]-2-phenyl-ethyl}-amide;

5-chloro-1H-indole-2-carboxylic acid ((1S)-{(R)-hydroxy-[methyl-(2-pyridin-2-yl-ethyl)-carbamoyl]-methyl}-2-phenyl-ethyl)-amide;

5-chloro-1H-indole-2-carboxylic acid [(1S)-benzyl-(2R)-hydroxy-3-(4-methyl-piperazin-1-yl)-3-oxo-propyl]-amide hydrochloride;

5-chloro-1H-indole-2-carboxylic acid [(1S)-benzyl-(2R)-hydroxy-3-(3-hydroxy-azetidin-1yl)-3-oxo-propyl]-amide;

5-chloro-1H-indole-2-carboxylic acid ((1S)-benzyl-(2R)-hydroxy-3-isoxazolidin-2-yl-3-oxo-propyl)-amide;

5-chloro-1H-indole-2-carboxylic acid ((1S)-benzyl-(2R)-hydroxy-3-[1,2]oxazinan-2-yl-3-oxo-propyl)-amide;

5-chloro-1H-indole-2-carboxylic acid [(1S)-benzyl-(2R)-hydroxy-3-((3S)-hydroxy-pyrrolidin-1-yl)-3-oxo-propyl]-amide;

5-chloro-1H-indole-2-carboxylic acid [(1S)-benzyl-3-((3S,4S)-dihydroxy-pyrrolidin-1yl)-(2R)-hydroxy-3-oxo-propyl]-amide;

5-chloro-1H-indole-2-carboxylic acid [(1S)-benzyl-3-(cis-3,4-dihydroxy-pyrrolidin-1yl)-(2R)-hydroxy-3-oxo-propyl]-amide;

5-chloro-1H-indole-2-carboxylic acid ((1S)-benzyl-(2R)-hydroxy-3-morpholin-4-yl-3-oxo-propyl)-amide;

5-chloro-1H-indole-2-carboxylic acid [(1S)-benzyl-2-(3-hydroxyimino-pyrrolidin-1yl)-2-oxo-ethyl]-amide;

5-chloro-1H-indole-2-carboxylic acid [2-(cis-3,4-dihydroxy-pyrrolidin-1yl)-2-oxo-ethyl]-amide;

5-chloro-1H-indole-2-carboxylic acid [2-((3S,4S)-dihydroxy-pyrrolidin-1yl)-2-oxo-ethyl]-amide;

5-chloro-1H-indole-2-carboxylic acid [(1S)-benzyl-2-(cis-3,4-dihydroxy-pyrrolidin-1yl)-2-oxo-ethyl]-amide;

5-chloro-1H-indole-2-carboxylic acid [2-(1,1-dioxo-thiazolidin-3-yl)-2-oxo-ethyl]-amide;

5-chloro-1H-indole-2-carboxylic acid (2-oxo-2-thiazolidin-3-yl-ethyl)-amide, 5-chloro-1H-indole-2-carboxylic acid [(1S)-(4-fluoro-benzyl)-2-(4-hydroxy-piperidin-1yl)-2-oxo-ethyl]-amide;

5-chloro-1H-indole-2-carboxylic acid [(1S)-benzyl-2-((3RS)-hydroxy-piperidin-1-yl)-2-oxo-ethyl]-amide;

5-chloro-1H-indole-2-carboxylic acid [2-oxo-2-((1 RS)-oxo-1-thiazolidin-3-yl)-ethyl]-amide;

5-chloro-1H-indole-2-carboxylic acid [(1S)-(2-fluoro-benzyl)-2-(4-hydroxy-piperidin-1yl)-2-oxo-ethyl]-amide;

5-chloro-1H-indole-2-carboxylic acid [(1S)-benzyl-2-((3S,4S)-dihydroxy-pyrrolidin-1yl)-2-oxo-ethyl]-amide;

5-chloro-1H-indole-2-carboxylic acid [(1S)-benzyl-2-(3-hydroxy-azetidin-1yl)-2-oxo-ethyl]-amide;

5-chloro-1H-indole-2-carboxylic acid [(1S)-benzyl-2-(3-hydroxyimino-azetidin-1yl)-2-oxo-ethyl]-amide;

5-chloro-1H-indole-2-carboxylic acid [(1S)-benzyl-2-(4-hydroxyimino-piperidin-1yl)-2-oxo-ethyl]-amide;

5-chloro-1H-indole-2-carboxylic acid [1-benzyl-2-(3-hydroxypyrrolidin-1yl)-2-oxo-ethyl]amide;

5-chloro-1H-indole-2-carboxylic acid [(1S)-((R)-hydroxy-dimethylcarbamoyl-methyl)-2-phenyl-ethyl]-amide;

5-chloro-1H-indole-2-carboxylic acid [(1S)-((R)-hydroxy-(methoxy-methyl-carbamoyl)-methyl)-2-phenyl-ethyl]-amide;

5-chloro-1H-indole-2-carboxylic acid [(1S)-benzyl-3-((3-hydroxy azetidin-1-yl)-(2R)-hydroxy-3-oxopropyl]-amide;

5-chloro-1H-indole-2-carboxylic acid [(1S)-((R)-hydroxy-[methyl-(2-hydroxyethyl)-carbamoyl]-methyl)-2-phenyl-ethyl]-amide;

5-chloro-1H-indole-2-carboxylic acid [(1S)-benzyl-(2R)-hydroxy-3-((3S)-hydroxy-pyrrolidin-1-yl)-3-oxopropyl]-amide;

5-chloro-1H-indole-2-carboxylic acid [(1S)-benzyl-(2R)-hydroxy-3-((3S,4S)-dihydroxy-pyrrolidin-1-yl)-3-oxopropyl]-amide;

5-chloro-1H-indole-2-carboxylic acid [(1S)-benzyl-3-(cis-3,4-dihydroxy-pyrrolidin-1yl)-(2R)-hydroxy-3-oxopropyl]-amide;

5-chloro-1H-indole-2-carboxylic acid [1-benzyl-2-(3-hydroxypyrrolidin-1yl)-2-oxo-ethyl]-amide;

5-chloro-1H-indole-2-carboxylic acid [(1S)-benzyl-2-(cis-3,4-dihydroxypyrrolidin-1yl)-2-oxo-ethyl]-amide;

5-chloro-1H-indole-2-carboxylic acid [(1S)-(4-fluorobenzyl-2-(4-hydroxy-piperidin-1yl)-2-oxo-ethyl]-amide;

5-chloro-1H-indole-2-carboxylic acid (2-oxo-2-thiazolidin-3-yl-ethyl)-amide;

5-chloro-1H-indole-2-carboxylic acid [(1S)-benzyl-2-(3-hydroxy-azetidin-1yl)-2-oxo-ethyl]-amide;

5-chloro-1H-indole-2-carboxylic acid [(1S)-benzyl-2-(3-hydroxyimino-azetidin-1yl)-2-oxo-ethyl]-amide;

5-chloro-1H-indole-2-carboxylic acid [(1S)-benzyl-2-((3S,4S)-dihydroxy-pyrrolidin-1-yl)-2-oxo-ethyl]-amide; and the pharmaceutically acceptable salts and prodrugs thereof, and salts of the prodrugs.

Any glycogen phosphorylase inhibitor may be used as a compound (active agent) in the combination aspect of the present invention. Glycogen phosphorylase inhibition is readily determined by those skilled in the art according to standard assays (for example, Pesce, et al. (1977) *Clinical Chemistry* 23:1711–1717). A variety of glycogen phosphorylase inhibitors are described above, however, other glycogen phosphorylase inhibitors will be known to those skilled in the art (e.g., WO 95/24391-A and those disclosed in U.S. Pat. No. 5,952,363). The following documents also disclose glycogen phosphorylase inhibitors that can be used in the present invention: U.S. Pat. No. 5,998,463; Oikanomakos et al., *Protein Science*, 1999 8(10) 1930–1945, which in particular discloses the compound 3-isopropyl-4-(2-chlorophenyl)-1,4-dihydro-1-ethyl-2-methylpyridine; WO 9524391; WO 9709040; WO 9840353; WO 9850359; WO 9731901; EP 884050; and Hoover et al., *J. Med. Chem.*, 1998, 41, 2934–2938.

A neurotensin receptor ligand can also be used in combination with an aldose reductase inhibitor. Aldose reductase inhibitors constitute a class of compounds that have become widely known for their utility in treating conditions arising from complications of diabetes, such as diabetic neuropathy and nephropathy. Such compounds are well known to those skilled in the art and are readily identified by standard biological tests. For example, the aldose reductase inhibitor zopolrestat, 1-phthalazineacetic acid, 3,4-dihydro-4-oxo-3-[[5-(trifluoromethyl)-2-benzothiazolyl]methyl]-, and related compounds are described in U.S. Pat. No. 4,939,140.

Aldose reductase inhibitors have been taught for use in lowering lipid levels in mammals. See, for example, U.S. Pat. No. 4,492,706 and EP 0 310 931 A2.

U.S. Pat. No. 5,064,830 discloses the use of certain oxophthalazinyl acetic acid aldose reductase inhibitors, including zopolrestat, for lowering of blood uric acid levels.

Commonly assigned U.S. Pat. No. 5,391,551 discloses the use of certain aldose reductase inhibitors, including zopolrestat, for lowering blood lipid levels in humans. The disclosure teaches that therapeutic utilities derive from the treatment of diseases caused by an increased level of triglycerides in the blood, such diseases include cardiovascular disorders such as thrombosis, arteriosclerosis, myocardial infarction, and angina pectoris. A preferred aldose reductase inhibitor is zopolrestat.

The term aldose reductase inhibitor refers to a compound that inhibits the bioconversion of glucose to sorbitol, which is catalyzed by the enzyme aldose reductase. Any aldose reductase inhibitor may be used in a combination with a neurotensin receptor ligand. Aldose reductase inhibition is readily determined by those skilled in the art according to standard assays (J. Malone, *Diabetes*, 29:861–864 (1980) "Red Cell Sorbitol, an Indicator of Diabetic Control"). A variety of aldose reductase inhibitors are described herein; however, other aldose reductase inhibitors useful in certain of the compositions and methods of this invention will be known to those skilled in the art.

The activity of an aldose reductase inhibitor in a tissue can be determined by testing the amount of aldose reductase inhibitor that is required to lower tissue sorbitol (i.e., by inhibiting the further production of sorbitol consequent to blocking aldose reductase) or lower tissue fructose (by inhibiting the production of sorbitol consequent to blocking aldose reductase and consequently the production of fructose.

Accordingly, examples of aldose reductase inhibitors useful in certain of the compositions, combinations and methods of the present invention include:

1. 3-(4-bromo-2-fluorobenzyl)-3,4-dihydro-4-oxo-1-phthalazineacetic acid (ponalrestat, U.S. Pat. No. 4,251,528);
2. N[[(5-trifluoromethyl)-6-methoxy-1-naphthalenyl]thioxomethyl]-N-methylglycine (tolrestat, U.S. Pat. No. 4,600,724);
3. 5-[(Z,E)-β-methylcinnamylidene]-4-oxo-2-thioxo-3-thiazolideneacetic acid (epalrestat, U.S. Pat. No. 4,464,382, U.S. Pat. No. 4,791,126, U.S. Pat. No. 4,831,045);
4. 3-(4-bromo-2-fluorobenzyl)-7-chloro-3,4-dihydro-2,4-dioxo-1(2H)-quinazolineacetic acid (zenarestat, U.S. Pat. Nos. 4,734,419, and 4,883,800);
5. 2R,4R-6,7-dichloro-4-hydroxy-2-methylchroman-4-acetic acid (U.S. Pat. No. 4,883,410);
6. 2R,4R-6,7-dichloro-6-fluoro-4-hydroxy-2-methylchroman-4-acetic acid (U.S. Pat. No. 4,883,410);
7. 3,4-dihydro-2,8-diisopropyl-3-oxo-2H-1,4-benzoxazine-4-acetic acid (U.S. Pat. No. 4,771,050);
8. 3,4-dihydro-3-oxo-4-[(4,5,7-trifluoro-2-benzothiazolyl)methyl]-2H-1,4-benzothiazine-2-acetic acid (SPR-210, U.S. Pat. No. 5,252,572);
9. N-[3,5-dimethyl-4-[(nitromethyl)sulfonyl]phenyl]-2-methyl-benzeneacetamide (ZD5522, U.S. Pat. Nos. 5,270,342 and 5,430,060);
10. (S)-6-fluorospiro[chroman-4,4'-imidazolidine]-2,5'-dione (sorbinil, U.S. Pat. No. 4,130,714);
11. d-2-methyl-6-fluoro-spiro(chroman-4',4'-imidazolidine)-2',5'-dione (U.S. Pat. No. 4,540,704);
12. 2-fluoro-spiro(9H-fluorene-9,4'-imidazolidine)2',5'-dione (U.S. Pat. No. 4,438,272);
13. 2,7-di-fluoro-spiro(9H-fluorene-9,4'-imidazolidine)2',5'-dione (U.S. Pat. Nos. 4,436,745, 4,438,272);
14. 2,7-di-fluoro-5-methoxy-spiro(9H-fluorene-9,4'-imidazolidine)2',5'-dione (U.S. Pat. Nos. 4,436,745, 4,438,272);
15. 7-fluoro-spiro(5H-indenol[1,2-b]pyridine-5,3'-pyrrolidin)2,5'-dione (U.S. Pat. Nos. 4,436,745, 4,438, 272);
16. d-cis-6'-chloro-2',3'-dihydro-2'-methyl-spiro-(imidazolidine-4,4'-4'-H-pyrano(2,3-b)pyridine)-2,5-dione (U.S. Pat. No. 4,980,357);
17. spiro[imidazolidine-4,5'(6H)-quinoline]2,5-dione-3'-chloro-7',8'-dihydro-7'-methyl-(5'-cis) (U.S. Pat. No. 5,066,659);
18. (2S,4S)-6-fluoro-2',5'-dioxospiro(chroman-4,4'-imidazolidine)-2-carboxamide (U.S. Pat. No. 5,447, 946);
19. 2-[(4-bromo-2-fluorophenyl)methyl]-6-fluorospiro [isoquinoline-4(1H),3'-pyrrolidine]-1,2',3,5'(2H)-tetrone (ARI-509, U.S. Pat. No. 5,037,831);
20. 3,4-dihydro-3-(5-fluorobenzothiazol-2-ylmethyl)-4-oxophthalazin-1-yl-acetic acid;
21. 3-(5,7-difluorobenzothiazol-2-ylmethyl)-3,4-dihydro-4-oxophthalazin-1-ylacetic acid;
22. 3-(5-chlorobenzothiazol-2-ylmethyl)-3,4-dihydro-4-oxophthalazin-1ylacetic acid;
23. 3-(5,7-dichlorobenzothiazol-2-ylmethyl)-3,4-dihydro-4-oxophthalazin-1-ylacetic acid;
24. 3,4-dihydro-4-oxo-3-(5-trifluoromethylbenzoxazol-2-ylmethyl)phthalazin-1-ylacetic acid;
25. 3,4-dihydro-3-(5-fluorobenzoxazol-2-ylmethyl)-4-oxophthalazin-1-yl-acetic acid;
26. 3-(5,7-difluorobenzoxazol-2-ylmethyl)-3,4-dihydro-4-oxophthalazin-1-ylacetic acid;
27. 3-(5-chlorobenzoxazol-2-ylmethyl)-3,4-dihydro-4-oxophthalazin-1-ylacetic acid;
28. 3-(5,7-dichlorobenzoxazol-2-ylmethyl)-3,4-dihydro-4-oxophthalazin-1-ylacetic acid;
29. zopolrestat; 1-phthalazineacetic acid, 3,4-dihydro-4-oxo-3-[[5-(trifluoromethyl)-2-benzothiazolyl]methyl]-; and the pharmaceutically acceptable salts and prodrugs thereof, and salts of the prodrugs.

Procedures for making the aldose reductase inhibitors 20–29 are disclosed in PCT publication number WO 99/26659.

A neurotensin receptor ligand can also be used in combination with a sorbitol dehydrogenase inhibitor. Sorbitol dehydrogenase inhibitors lower fructose levels and have been used to treat or prevent diabetic complications such as neuropathy, retinopathy, nephropathy, cardiomyopathy, microangiopathy, and macroangiopathy. U.S. Pat. Nos. 5,728,704 and 5,866,578 disclose compounds and methods for treating diabetic complications by inhibiting the enzyme sorbitol dehydrogenase. The compounds disclosed in these patents and other sorbitol dehydrogenase inhibitors can be used in the present invention in combination with a neurotensin receptor ligand.

A neurotensin receptor ligand can also be used in combination with a glucocorticoid receptor antagonist. The glucocorticoid receptor (GR) is present in glucocorticoid responsive cells where it resides in the cytosol in an inactive state until it is stimulated by an agonist. Upon stimulation the glucocorticoid receptor translocates to the cell nucleus where it specifically interacts with DNA and/or protein(s) and regulates transcription in a glucocorticoid responsive manner. Two examples of proteins that interact with the glucocorticoid receptor are the transcription factors, API and NF$_\kappa$-β. Such interactions result in inhibition of API- and NF$_\kappa$-β-mediated transcription and are believed to be responsible for the anti-inflammatory activity of endogenously administered glucocorticoids. In addition, glucocorticoids may also exert physiologic effects independent of nuclear transcription. Biologically relevant glucocorticoid receptor agonists include cortisol and corticosterone. Many synthetic glucocorticoid receptor agonists exist including dexamethasone, prednisone and prednisilone. By definition, glucocorticoid receptor antagonists bind to the receptor and prevent glucocorticoid receptor agonists from binding and eliciting GR mediated events, including transcription. RU486 is an example of a non-selective glucocorticoid receptor antagonist. GR antagonists can be used in the treatment of diseases associated with an excess or a deficiency of glucocorticoids in the body. As such, they may be used to treat the following: obesity, diabetes, cardiovascular disease, hypertension, Syndrome X, depression, anxiety, glaucoma, human immunodeficiency virus (HIV) or acquired immunodeficiency syndrome (AIDS), neurodegeneration (for example, Alzheimer's and Parkinson's), cognition enhancement, Cushing's Syndrome, Addison's Disease, osteoporosis, frailty, inflammatory diseases (such as osteoarthritis, rheumatoid arthritis, asthma and rhinitis), adrenal dysfunction, viral infection, immunodeficiency, immunomodulation, autoimmune diseases, allergies, wound healing, compulsive behavior, multi-drug resistance, addiction, psychosis, anorexia, cachexia, post-traumatic stress syndrome, post-surgical bone fracture, medical catabolism and prevention of muscle frailty.

Examples of preferred glucocorticoid receptor antagonists that can be used in combination with a neurotensin receptor ligand can be found in U.S. provisional patent application No. 60/132,130.

A neurotensin receptor ligand can also be used in combination with a sodium-hydrogen exchanger type 1 (NHE-1) inhibitor. Preferred NHE-1 inhibitors that can be used in combination with a neurotensin receptor ligand can be found in PCT publication number WO 99/43663.

In addition, a neurotensin receptor ligand can be used in combination with a thyromimetic. It is generally accepted that thyroid hormones, specifically, biologically active iodothyronines, are critical to normal development and to maintaining metabolic homeostasis. Thyroid hormones stimulate the metabolism of cholesterol to bile acids and enhance the lipolytic responses of fat cells to other hormones. U.S. Pat. Nos. 4,766,121; 4,826,876; 4,910,305; and 5,061,798 disclose certain thyroid hormone mimetics (thyromimetics), namely, 3,5-dibromo-3'-[6-oxo-3(1H)-pyridazinylmethyl]-thyronines. U.S. Pat. No. 5,284,971 discloses certain thyromimetic cholesterol lowering agents, namely, 4-(3-cyclohexyl-4-hydroxy or -methoxy phenylsulfonyl)-3,5 dibromo-phenylacetic compounds. U.S. Pat. Nos. 5,401,772; 5,654,468; and 5,569,674 disclose certain thyromimetics that are lipid lowering agents, namely, heteroacetic acid derivatives. In addition, certain oxamic acid derivatives of thyroid hormones are known in the art. For example, N. Yokoyama, et al. in an article published in the *Journal of Medicinal Chemistry*, 38 (4): 695–707 (1995) describe replacing a —$CH_2$ group in a naturally occurring metabolite of $T_3$ with an —NH group resulting in —$HNCOCO_2H$. Likewise, R. E. Steele et al. in an article published in International Congressional Service (*Atherosclerosis* X) 1066: 321–324 (1995) and Z. F. Stephan et al. in an article published in *Atherosclerosis*, 126: 53–63 (1996), describe certain oxamic acid derivatives that are useful as lipid-lowering thyromimetic agents and are devoid of undesirable cardiac activities.

In addition, a neurotensin receptor ligand can be administered in combination with other pharmaceutical agents such as cholesterol biosynthesis inhibitors and cholesterol absorption inhibitors, especially HMG-CoA reductase inhibitors and HMG-CoA synthase inhibitors, HMG-CoA reductase and synthase gene expression inhibitors, CETP inhibitors, bile acid sequesterants, fibrates, ACAT inhibitors, squalene synthetase inhibitors, anti-oxidants and niacin. A neurotensin receptor ligand may also be administered in combination with naturally occurring compounds that act to lower plasma cholesterol levels. These naturally occurring compounds are commonly called nutraceuticals and include, for example, garlic extract, Benecol®, and niacin.

Specific cholesterol absorption inhibitors and cholesterol biosynthesis inhibitors are described in detail below. Additional cholesterol absorption inhibitors are known to those skilled in the art and are described, for example, in WO 94/00480.

Any HMG-CoA reductase inhibitor may be employed as an additional compound in the combination therapy aspect of the present invention. The term HMG-CoA reductase inhibitor refers to a compound that inhibits the biotransformation of hydroxymethylglutaryl-coenzyme A to mevalonic acid as catalyzed by the enzyme HMG-CoA reductase. Such inhibition may be determined readily by one of skill in the art according to standard assays (e.g., *Methods of Enzymology*, 71: 455–509 (1981); and the references cited therein). A variety of these compounds are described and referenced below. U.S. Pat. No. 4,231,938 discloses certain compounds isolated after cultivation of a microorganism belonging to the genus Aspergillus, such as lovastatin. Also, U.S. Pat. No. 4,444,784 discloses synthetic derivatives of the aforementioned compounds, such as simvastatin. Additionally, U.S. Pat. No. 4,739,073 discloses certain substituted indoles, such as fluvastatin. Further, U.S. Pat. No. 4,346,227 discloses ML-236B derivatives, such as pravastatin. In addition, EP 491,226 teaches certain pyridyldihydroxyheptenoic acids, such as rivastatin. Also, U.S. Pat. No. 4,647,576 discloses certain 6-[2-(substituted-pyrrol-1-yl)-alkyl]-pyran-2-ones such as atorvastatin. Other HMG-CoA reductase inhibitors will be known to those skilled in the art. Examples of marketed products containing HMG-CoA reductase inhibitors that can be used in combination with compounds of the present invention include Baycol®, Lescol®, Lipitor®, Mevacor®, Pravachol® and Zocor®.

Any HMG-CoA synthase inhibitor may be used as the second compound in the combination therapy aspect of this invention. The term HMG-CoA synthase inhibitor refers to a compound which inhibits the biosynthesis of hydroxymethylglutaryl-coenzyme A from acetyl-coenzyme A and acetoacetyl-coenzyme A, catalyzed by the enzyme HMG-CoA synthase. Such inhibition may be determined readily by one of skill in the art according to standard assays (e.g., *Methods of Enzymology*, 35: 155–160 (1975); and *Methods of Enzymology*, 110: 19–26 (1985); and the references cited therein). A variety of these compounds are described and referenced below. U.S. Pat. No. 5,120,729 discloses certain beta-lactam derivatives. U.S. Pat. No. 5,064,856 discloses certain spiro-lactone derivatives prepared by culturing the microorganism MF5253. U.S. Pat. No. 4,847,271 discloses certain oxetane compounds such as 11-(3-hydroxymethyl-4-oxo-2-oxetayl)-3,5,7-trimethyl-2,4-undecadienoic acid derivatives. Other HMG-COA synthase inhibitors will be known to those skilled in the art.

Any compound that decreases HMG-COA reductase gene expression may be used as an additional compound in the combination therapy aspect of this invention. These agents may be HMG-CoA reductase transcription inhibitors that block the transcription of DNA or translation inhibitors that prevent translation of mRNA coding for HMG-CoA reductase into protein. Such inhibitors may either affect transcription or translation directly, or may be biotransformed into compounds that have the aforementioned attributes by one or more enzymes in the cholesterol biosynthetic cascade or may lead to the accumulation of an isoprene metabolite that has the aforementioned activities. Such regulation is readily determined by those skilled in the art according to standard assays (*Methods of Enzymology*, 110: 9–19 1985). Several such compounds are described and referenced below however other inhibitors of HMG-CoA reductase gene expression will be known to those skilled in the art. U.S. Pat. No. 5,041,432 discloses certain 15-substituted lanosterol derivatives. Other oxygenated sterols that suppress the biosynthesis of HMG-CoA reductase are discussed by E. I. Mercer (*Prog. Lip. Res.*, 32:357–416 1993).

Any compound having activity as a CETP inhibitor can serve as the second compound in the combination therapy aspect of the instant invention. The term CETP inhibitor refers to compounds that inhibit the cholesteryl ester transfer protein (CETP) mediated transport of various cholesteryl esters and triglycerides from HDL to LDL and VLDL. A variety of these compounds are described and referenced below however other CETP inhibitors will be known to those skilled in the art. U.S. Pat. No. 5,512,548 discloses certain polypeptide derivatives having activity as CETP inhibitors, while certain CETP-inhibitory rosenonolactone derivatives and phosphate-containing analogs of cholesteryl ester are disclosed in *J. Antibiot.*, 49(8): 815–816 (1996), and *Bioorg. Med. Chem. Lett.*; 6:1951–1954 (1996), respectively. Other CETP inhibitors that can be used in combination with a neurotensin receptor ligand are disclosed in WO 99/20302, EP 796846, EP818197, EP 818448, WO 99/14204, WO 99/41237, WO 95/04755, WO 96/15141, WO 96/05227, DE 19704244, DE19741051, DE 19741399, DE 19704243, DE 19709125, DE 19627430, DE 19832159, DE 19741400, JP 11049743, and JP 09059155. Preferred CETP inhibitors that can be used in combination with a neurotensin receptor ligand include:

[2R,4S] 4-[(3,5-bis-trifluoromethyl-benzyl)-methoxycarbonyl-amino]-2-ethyl-6-trifluoromethyl-3,4-dihydro-2H-quinoline-1-carboxylic acid isopropyl ester;

[2S,4S] 4-[(3,5-bis-trifluoromethyl-benzyl)-methoxycarbonyl-amino]-2-methoxymethyl-6-trifluoromethyl-3,4-dihydro-2H-quinoline-1-carboxylic acid isopropyl ester;

[2R,4S] 4-[(3,5-bis-trifluoromethyl-benzyl)-methoxycarbonyl-amino]-2-ethyl-6-trifluoromethyl-3,4-dihydro-2H-quinoline-1-carboxylic acid 2-hydroxyethyl ester;

[2S,4S] 4-[(3,5-bis-trifluoromethyl-benzyl)-methoxycarbonyl-amino]-2-cyclopropyl-6-trifluoromethyl-3,4-dihydro-2H-quinoline-1-carboxylic acid ethyl ester;

[2R,4S] 4-[(3,5-bis-trifluoromethyl-benzyl)-methoxycarbonyl-amino]-2-ethyl-6-trifluoromethyl-3,4-dihydro-2H-quinoline-1-carboxylic acid ethyl ester;

[2S,4S] 4-[(3,5-bis-trifluoromethyl-benzyl)-methoxycarbonyl-amino]-2-cyclopropyl-6-trifluoromethyl-3,4-dihydro-2H-quinoline-1-carboxylic acid propyl ester;

[2R,4S] 4-[(3,5-bis-trifluoromethyl-benzyl)-methoxycarbonyl-amino]-2-ethyl-6-trifluoromethyl-3,4-dihydro-2H-quinoline-1-carboxylic acid propyl ester;

[2S,4S] 4-[(3,5-bis-trifluoromethyl-benzyl)-methoxycarbonyl-amino]-2-isopropyl-6-trifluoromethyl-3,4-dihydro-2H-quinoline-1-carboxylic acid isopropyl ester;

[2S,4S] 4-[(3,5-bis-trifluoromethyl-benzyl)-methoxycarbonyl-amino]-6-chloro-2-cyclopropyl-3,4-dihydro-2H-quinoline-1-carboxylic acid isopropyl ester;

[2S,4S] 2-cyclopropyl-4-[(3,5-dichloro-benzyl)-methoxycarbonyl-amino]-6-trifluoromethyl-3,4-dihydro-2H-quinoline-1-carboxylic acid isopropyl ester;

[2S,4S] 4-[(3,5-bis-trifluoromethyl-benzyl)-methoxycarbonyl-amino]-2-cyclopropyl-6-trifluoromethyl-3,4-dihydro-2H-quinoline-1-carboxylic acid tert-butyl ester;

[2S,4S] 4-[(3,5-bis-trifluoromethyl-benzyl)-methoxycarbonyl-amino]-2-cyclopropyl-6-trifluoromethyl-3,4-dihydro-2H-quinoline-1-carboxylic acid isopropyl ester;

[2S,4S] 4-[(3,5-bis-trifluoromethyl-benzyl)-methoxycarbonyl-amino]-2-cyclobutyl-6-trifluoromethyl-3,4-dihydro-2H-quinoline-1-carboxylic acid isopropyl ester;

[2R,4S] 4-[(3,5-bis-trifluoromethyl-benzyl)-methoxycarbonyl-amino]-2-ethyl-6-trifluoromethyl-3,4-dihydro-2H-quinoline-1-carboxylic acid isopropyl ester;

[2S,4S] 4-[(3,5-bis-trifluoromethyl-benzyl)-methoxycarbonyl-amino]-2-methoxymethyl-6-trifluoromethyl-3,4-dihydro-2H-quinoline-1-carboxylic acid isopropyl ester;

[2R,4S] 4-[(3,5-bis-trifluoromethyl-benzyl)-methoxycarbonyl-amino]-2-ethyl-6-trifluoromethyl-3,4-dihydro-2H-quinoline-1-carboxylic acid 2-hydroxyethyl ester;

[2S,4S] 4-[(3,5-bis-trifluoromethyl-benzyl)-methoxycarbonyl-amino]-2-cyclopropyl-6-trifluoromethyl-3,4-dihydro-2H-quinoline-1-carboxylic acid ethyl ester;

[2R,4S] 4-[(3,5-bis-trifluoromethyl-benzyl)-methoxycarbonyl-amino]-2-ethyl-6-trifluoromethyl-3,4-dihydro-2H-quinoline-1-carboxylic acid ethyl ester;

[2S,4S] 4-[(3,5-bis-trifluoromethyl-benzyl)-methoxycarbonyl-amino]-2-cyclopropyl-6-trifluoromethyl-3,4-dihydro-2H-quinoline-1-carboxylic acid propyl ester;

[2R,4S] 4-[(3,5-bis-trifluoromethyl-benzyl)-methoxycarbonyl-amino]-2-ethyl-6-trifluoromethyl-3,4-dihydro-2H-quinoline-1-carboxylic acid propyl ester; and the pharmaceutically acceptable salts and prodrugs thereof, and the salts of the prodrugs.

Any ACAT inhibitor can serve as an additional compound in the combination therapy aspect of this invention. The term ACAT inhibitor refers to a compound that inhibits the intracellular esterification of dietary cholesterol by the enzyme acyl CoA: cholesterol acyltransferase. Such inhibition may be determined readily by one of skill in the art according to standard assays, such as the method of Heider et al. described in *Journal of Lipid Research.*, 24:1127 (1983). A variety of these compounds are described and referenced below; however, other ACAT inhibitors will be known to those skilled in the art. U.S. Pat. No. 5,510,379 discloses certain carboxysulfonates, while WO 96/26948 and WO 96/10559 both disclose urea derivatives having ACAT inhibitory activity.

Any compound having activity as a squalene synthetase inhibitor can serve as an additional compound in the combination therapy aspect of the instant invention. The term squalene synthetase inhibitor refers to a compound that inhibits the condensation of two molecules of farnesylpyrophosphate to form squalene, a reaction that is catalyzed by the enzyme squalene synthetase. Such inhibition is readily determined by those skilled in the art according to standard methodology (*Methods of Enzymology*, 15:393–454 (1969); and *Methods of Enzymology*, 110: 359–373 (1985); and references cited therein). A summary of squalene synthetase inhibitors has been complied in *Curr. Op.Ther. Patents*, 861–4, (1993). European patent application publication number 0 567 026 A1 discloses certain 4,1-benzoxazepine derivatives as squalene synthetase inhibitors and their use in the treatment of hypercholesterolemia and as fungicides. European patent application publication number 0 645 378 A1 discloses certain seven- or eight-membered heterocycles as squalene synthetase inhibitors and their use in the treatment and prevention of hypercholesterolemia and fungal infections. European patent application publication number 0 645 377 A1 discloses certain benzoxazepine derivatives as squalene synthetase inhibitors useful for the treatment of hypercholesterolemia or coronary sclerosis. European patent application publication number 0 611 749 A1 discloses certain substituted amic acid derivatives useful for the treatment of arteriosclerosis. European patent application publication number 0 705 607 A2 discloses certain condensed seven- or eight-membered heterocyclic compounds useful as antihypertriglyceridemic agents. PCT publication WO 96/09827 discloses certain combinations of cholesterol absorption inhibitors and cholesterol biosynthesis inhibitors including benzoxazepine derivatives and benzothiazepine derivatives. European patent application publication number 0 701 725 A1 discloses a process for preparing certain optically-active compounds, including benzoxazepine derivatives, having plasma cholesterol and triglyceride lowering activities. Other compounds that are marketed for hyperlipidemia, including hypercholesterolemia and which are intended to help prevent or treat atherosclerosis include bile acid sequestrants, such as Colestid®, LoCholest® and Questran®; and fibric acid derivatives, such as Atromid®, Lopid® and Tricor®. These compounds can also be used in combination with a neurotensin receptor ligand.

It is also contemplated that a neurotensin receptor ligand be administered with a lipase inhibitor and/or a glucosidase inhibitor, which are typically used in the treatment of conditions resulting from the presence of excess triglycerides, free fatty acids, cholesterol, cholesterol esters or glucose including, inter alia, obesity, hyperlipidemia, hyperlipoproteinemia, Syndrome X, and the like.

In a combination with a neurotensin receptor ligand, any lipase inhibitor or glucosidase inhibitor may be employed. Preferred lipase inhibitors comprise gastric or pancreatic lipase inhibitors such as orlistat. Preferred glucosidase inhibitors comprise amylase inhibitors.

A lipase inhibitor is a compound that inhibits the metabolic cleavage of dietary triglycerides into free fatty acids and monoglycerides. Under normal physiological conditions, lipolysis occurs via a two-step process that involves acylation of an activated serine moiety of the lipase enzyme. This leads to the production of a fatty acid-lipase hemiacetal intermediate, which is then cleaved to release a diglyceride. Following further deacylation, the lipase-fatty acid intermediate is cleaved, resulting in free lipase, a monoglyceride and a fatty acid. The resultant free fatty acids and monoglycerides are incorporated into bile acid-phospholipid micelles, which are subsequently absorbed at the level of the brush border of the small intestine. The micelles eventually enter the peripheral circulation as chylomicrons. Accordingly, compounds, including lipase inhibitors that selectively limit or inhibit the absorption of ingested fat precursors are useful in the treatment of conditions including obesity, hyperlipidemia, hyperlipoproteinemia, Syndrome X, and the like.

Pancreatic lipase mediates the metabolic cleavage of fatty acids from triglycerides at the 1- and 3-carbon positions. The primary site of the metabolism of ingested fats is in the duodenum and proximal jejunum by pancreatic lipase, which is usually secreted in vast excess of the amounts necessary for the breakdown of fats in the upper small intestine. Because pancreatic lipase is the primary enzyme required for the absorption of dietary triglycerides, inhibitors have utility in the treatment of obesity and the other related conditions.

Gastric lipase is an immunologically distinct lipase that is responsible for approximately 10 to 40% of the digestion of dietary fats. Gastric lipase is secreted in response to mechanical stimulation, ingestion of food, the presence of a fatty meal or by sympathetic agents. Gastric lipolysis of ingested fats is of physiological importance in the provision of fatty acids needed to trigger pancreatic lipase activity in the intestine and is also of importance for fat absorption in a variety of physiological and pathological conditions associated with pancreatic insufficiency. See, for example, C. K. Abrams, et al., *Gastroenterology*, 92, 125 (1987).

A variety of lipase inhibitors are known to one of ordinary skill in the art. However, in the practice of certain of the methods, pharmaceutical compositions and kits of the instant invention, generally preferred lipase inhibitors are those inhibitors that are selected from the group consisting of lipstatin, tetrahydrolipstatin (orlistat), FL-386, WAY-121898, Bay-N-3176, valilactone, esterastin, ebelactone A, ebelactone B and RHC 80267.

The pancreatic lipase inhibitors lipstatin, 2S, 3S, 5S, 7Z, 10Z)-5-[(S)-2-formamido-4-methyl-valeryloxy]-2-hexyl-3-hydroxy-7,10-hexadecanoic acid lactone, and tetrahydrolipstatin (orlistat), 2S, 3S, 5S)-5-[(S)-2-formamido-4-methyl-valeryloxy]-2-hexyl-3-hydroxy-hexadecanoic acid lactone, and the variously substituted N-formylleucine derivatives and stereoisomers thereof, are disclosed in U.S. Pat. No. 4,598,089.

The pancreatic lipase inhibitor FL-386, 1-[4-(2-methylpropyl)cyclohexyl]-2-[(phenylsulfonyl)oxy]-ethanone, and the variously substituted sulfonate derivatives related thereto, are disclosed in U.S. Pat. No. 4,452,813.

The pancreatic lipase inhibitor WAY-121898, 4-phenoxyphenyl-4-methylpiperidin-1-yl-carboxylate, and the various carbamate esters and pharmaceutically acceptable salts related thereto, are disclosed in U.S. Pat. Nos. 5,512,565; 5,391,571 and 5,602,151.

The lipase inhibitor Bay-N-3176, N-3-trifluoromethylphenyl-N'-3-chloro-4'-trifluoromethylphenylurea, and the various urea derivatives related thereto, are disclosed in U.S. Pat. No. 4,405,644.

The pancreatic lipase inhibitor valilactone, and a process for the preparation thereof by the microbial cultivation of Actinomycetes strain MG147-CF2, are disclosed in Kitahara, et al., *J. Antibiotics*, 40 (11), 1647–1650 (1987).

The lipase inhibitor esteracin, and certain processes for the preparation thereof by the microbial cultivation of Streptomyces strain ATCC 31336, are disclosed in U.S. Pat. Nos. 4,189,438 and 4,242,453.

The pancreatic lipase inhibitors ebelactone A and ebelactone B, and a process for the preparation thereof by the microbial cultivation of Actinomycetes strain MG7-G1, are disclosed in Umezawa, et al., *J. Antibiotics*, 33, 1594–1596 (1980). The use of ebelactones A and B in the suppression of monoglyceride formation is disclosed in Japanese Kokai 08-143457, published Jun. 4, 1996.

The lipase inhibitor RHC 80267, cyclo-O,O'-[(1,6-hexanediyl)-bis-(iminocarbonyl)]dioxime, and the various bis(iminocarbonyl)dioximes related thereto may be prepared as described in Petersen et al., *Liebig's Annalen*, 562, 205–229 (1949). The ability of RHC 80267 to inhibit the activity of myocardial lipoprotein lipase is disclosed in Carroll et al., *Lipids*, 27, pp. 305–307 (1992) and Chuang et al., *J. Mol. Cell Cardiol.*, 22, 1009–1016 (1990).

A glucosidase inhibitor inhibits the enzymatic hydrolysis of complex carbohydrates by glycoside hydrolases, for example amylase or maltase, into bioavailable simple sugars, for example, glucose. The rapid metabolic action of glucosidases, particularly following the intake of high levels of carbohydrates, results in a state of alimentary hyperglycemia which, in adipose or diabetic subjects, leads to enhanced secretion of insulin, increased fat synthesis and a reduction in fat degradation. Following such hyperglycemias, hypoglycemia frequently occurs, due to the augmented levels of insulin present. Additionally, it is known that both hypoglycemias and chyme remaining in the stomach promotes the production of gastric juice, which initiates or favors the development of gastritis or duodenal ulcers. Accordingly, glucosidase inhibitors are known to have utility in accelerating the passage of carbohydrates through the stomach and inhibiting the absorption of glucose from the intestine. Furthermore, the conversion of carbohydrates into lipids of fatty tissue and the subsequent incorporation of alimentary fat into fatty tissue deposits is accordingly reduced or delayed, with the concomitant benefit of reducing or preventing the deleterious abnormalities resulting therefrom.

In combination with a neurotensin receptor ligand, any glucosidase inhibitor may be employed; however, a generally preferred glucosidase inhibitor comprises an amylase inhibitor. An amylase inhibitor is a glucosidase inhibitor that inhibits the enzymatic degradation of starch or glycogen into maltose. The inhibition of such enzymatic degradation is beneficial in reducing amounts of bioavailable sugars, including glucose and maltose, and the concomitant deleterious conditions resulting therefrom.

A variety of glucosidase and amylase inhibitors are known to one of ordinary skill in the art. However, in the practice of the methods and pharmaceutical compositions of the instant invention, generally preferred glucosidase inhibitors are those inhibitors that are selected from the group consisting of acarbose, adiposine, voglibose, miglitol, emiglitate, MDL-25637, camiglibose, tendamistate, AI-3688, trestatin, pradimicin-Q and salbostatin.

The glucosidase inhibitor acarbose, O-4,6-dideoxy-4-[[(1S,4R,5S,6S)-4,5,6-trihydroxy-3-(hydroxymethyl)-2-cyclohexen-1yl]amino]-α-glucopyranosyl-(1→4)-O-α-D-glucopyranosyl-(1→4)-D-glucose, the various amino sugar derivatives related thereto and a process for the preparation thereof by the microbial cultivation of Actinoplanes strains SE 50 (CBS 961.70), SB 18 (CBS 957.70), SE 82 (CBS 615.71), SE 50/13 (614.71) and SE 50/110 (674.73) are disclosed in U.S. Pat. Nos. 4,062,950 and 4,174,439 respectively.

The glucosidase inhibitor adiposine, consisting of adiposine forms 1 and 2, is disclosed in U.S. Pat. No. 4,254, 256. Additionally, a process for the preparation and purification of adiposine is disclosed in Namiki et al., *J. Antiobiotics*, 35, 1234–1236 (1982).

The glucosidase inhibitor voglibose, 3,4-dideoxy-4-[[2-hydroxy-1-(hydroxymethyl)ethyl]amino]-2-C-(hydroxymethyl)-D-epi-inositol, and the various N-substituted pseudo-aminosugars related thereto, are disclosed in U.S. Pat. No. 4,701,559.

The glucosidase inhibitor miglitol, (2R,3R,4R,5S)-1-(2-hydroxyethyl)-2-(hydroxymethyl)-3,4,5-piperidinetriol, and the various 3,4,5-trihydroxypiperidines related thereto, are disclosed in U.S. Pat. No. 4,639,436.

The glucosidase inhibitor emiglitate, ethyl p-[2-[(2R,3R, 4R,5S)-3,4,5-trihydroxy-2-(hydroxymethyl)piperidino] ethoxy]-benzoate, the various derivatives related thereto and pharmaceutically acceptable acid addition salts thereof, are disclosed in U.S. Pat. No. 5,192,772.

The glucosidase inhibitor MDL-25637, 2,6-dideoxy-7-O-β-D-glucopyrano-syl-2,6-imino-D-glycero-L-gluco-heptitol, the various homodisaccharides related thereto and the pharmaceutically acceptable acid addition salts thereof, are disclosed in U.S. Pat. No. 4,634,765.

The glucosidase inhibitor camiglibose, methyl 6-deoxy-6-[(2R,3R,4R,5S)-3,4,5-trihydroxy-2-(hydroxymethyl) piperidino]-α-D-glucopyranoside sesquihydrate, the deoxynojirimycin derivatives related thereto, the various pharmaceutically acceptable salts thereof and synthetic methods for the preparation thereof, are disclosed in U.S. Pat. Nos. 5,157,116 and 5,504,078.

The amylase inhibitor tendamistat, the various cyclic peptides related thereto and processes for the preparation thereof by the microbial cultivation of *Streptomyces tendae* strains 4158 or HAG 1226, are disclosed in U.S. Pat. No. 4,451,455.

The amylase inhibitor AI-3688, the various cyclic polypeptides related thereto, and a process for the preparation thereof by the microbial cultivation of *Streptomyces aureofaciens* strain FH 1656, are disclosed in U.S. Pat. No. 4,623,714.

The amylase inhibitor trestatin, consisting of a mixture of trestatin A, trestatin B and trestatin C, the various trehalose-containing aminosugars related thereto and a process for the preparation thereof by the microbial cultivation of *Streptomyces dimorphogenes* strains NR-320-OM7HB and NR-320-OM7HBS, are disclosed in U.S. Pat. No. 4,273, 765.

The glucosidase inhibitor pradimicin-Q and a process for the preparation thereof by the microbial cultivation of *Actinomadura verrucospora* strains R103-3 or A10102, are disclosed in U.S. Pat. Nos. 5,091,418 and 5,217,877, respectively.

The glycosidase inhibitor salbostatin, the various pseudosaccharides related thereto, the various pharmaceutically acceptable salts thereof and a process for the preparation thereof by the microbial cultivation of *Streptomyces albus* strain ATCC 21838, are disclosed in U.S. Pat. No. 5,091, 524.

Preferred lipase inhibitors comprise compounds selected from the group consisting of lipstatin, tetrahydrolipstatin, FL-386, WAY-121898, Bay-n-3176, valilactone, esteracin, ebelactone A, ebelactone B, RHC 80267, stereoisomers thereof, and pharmaceutically acceptable salts of said compounds and stereoisomers. The compound tetrahydrolipstatin is especially preferred.

Preferred glucosidase inhibitors comprise compounds selected from the group consisting of acarbose, adiposine, voglibose, miglitol, emiglitate, MDL-25637, camiglibose, pradimicin-Q, and salbostatin. An especially preferred glucosidase inhibitor is acarbose. Especially preferred glucosidase inhibitors further comprise amylase inhibitors that are selected from the group consisting of tendamistate, AI-3688 and trestatin.

In addition, the present invention includes the use of a neurotensin receptor ligand in combination with apo B secretion/MTP inhibitors.

A variety of apo B secretion/MTP inhibitors are known to one of ordinary skill in the art. Although any apo B secretion/MTP inhibitor may be used in the practice of the methods and pharmaceutical compositions of the instant invention, generally preferred apo B secretion/MTP inhibitors include those compounds that are disclosed in, for example, European patent application publication numbers EP 643057, EP 719763, EP 753517, EP 764647, EP 765878, EP 779276, EP 779279, EP 799828, EP 799829, EP 802186, EP 802188, EP 802192, and EP 802197; PCT Application Publication Numbers WO 96/13499, WO 96/33193, WO 96/40640, WO 97/26240, WO 97/43255, WO 97/43257, WO 98/16526 and WO 98/23593; and U.S. Pat. Nos. 5,595, 872; 5,646,162; 5,684,014; 5,712,279; 5,739,135 and 5,789, 197.

Especially preferred apo-B secretion/MTP inhibitors are those biphenyl-2-carboxylic acid-tetrahydroisoquinolin-6-yl amide derivatives disclosed in PCT application publication numbers WO 96/40640 and WO 98/23593. Especially preferred apo B secretion/MTP inhibitors disclosed in PCT application publication numbers WO 96/40640 and WO 98/23593, and useful in the methods and pharmaceutical compositions of the present invention, are 4'-trifluoromethyl-biphenyl-2-carboxylic acid-[2-(1H-[1,2, 4]triazol-3-ylmethyl)-1,2,3,4-tetrahydroisoquin-6-yl]-amide and 4'-trifluoromethyl-biphenyl-2-carboxylic acid-[2-(acetylaminoethyl)-1,2,3,4-tetrahydroisoquinolin-6-yl]-amide.

Another especially preferred class of apo B secretion/ MTP inhibitors is disclosed in U.S. Pat. Nos. 5,595,872; 5,721,279; 5,739,135 and 5,789,197.

Especially preferred apo B secretion/MTP inhibitors disclosed in U.S. Pat. Nos. 5,595,872; 5,721,279; 5,739,135 and 5,789,197 and useful in the methods and pharmaceutical compositions of the present invention, are 9-(4-{4-[4'trifluoromethyl-biphenyl-2-carbonyl)-amino]-piperidin-1yl}-butyl-9H-fluorene-9-carboxylic acid-(2,2,2-trifluoroethyl)-amide and 9-{4-[4-(2-benzothiazol-2-yl-benzoylamino)-piperidin-1-yl]-butyl}-9H-fluorene-9-carboxylic acid-(2,2,2-trifluoroethyl)-amide.

Another class of especially preferred apo B secretion/ MTP inhibitors is disclosed in PCT application publication number WO 98/16526.

Especially preferred apo B secretion/MTP inhibitors disclosed in PCT application publication number WO 98/16526, and useful in the methods and pharmaceutical compositions of the present invention, are [11a-R]-8-[(4-cyanophenyl)methoxy]-2-cyclopentyl-7-(prop-2-enyl)-2,3, 11,11a-tetrahydro-6H-pyrazino[1,2b]isoquinoline-1,4-dione and [11a-R]-cyclopentyl-7-(prop-2-enyl)-8-[(pyridin-2-yl) methoxy]-2,3,11,11a-tetrahydro-6H-pyrazino[1,2b] isoquinoline-1,4-dione.

Another especially preferred class of apo B secretion/ MTP inhibitors is disclosed in U.S. Pat. No. 5,684,014.

An especially preferred apo B secretion/MTP inhibitor disclosed in U.S. Pat. No. 5,684,014, and useful in certain of the methods and pharmaceutical compositions of the present invention, is 2-cyclopentyl-2-[4-(2,4-dimethyl-pyrido[2,3-b]indol-9-ylmethyl)-phenyl]-N-(2-hydroxy-1-phenyl-ethyl)-acetamide.

Yet another class of especially preferred apo B secretion/ MTP inhibitors is disclosed in U.S. Pat. No. 5,646,162.

An especially preferred apo B secretion/MTP inhibitor disclosed in U.S. Pat. No. 5,646,162 and useful in the methods and pharmaceutical compositions of the present invention, is 2-cyclopentyl-N-(2-hydroxy-1-phenylethyl)-2-[4-(quinolin-2-ylmethoxy)-phenyl]-acetamide.

Additional apo B secretion/MTP inhibitors that can be used in combination with a neurotensin receptor ligand are disclosed in U.S. provisional patent application No. 60/164, 803. Examples of specific preferred apo B secretion/MTP inhibitors disclosed in that application include:

7-amino-quinoline-3-carboxylic acid ethyl ester;
7-[(4'-trifluoromethyl-biphenyl-2-carbonyl)-amino]-quinoline-3-carboxylic acid ethyl ester;
7-[(4'-trifluoromethyl-biphenyl-2-carbonyl)-amino]-quinoline-3-carboxylic acid;
7-[(4'-trifluoromethyl-biphenyl-2-carbonyl)-amino]-quinoline-3-carboxylic acid (dipyridin-2-yl-methyl)-amide;
7-[(4'-trifluoromethyl-biphenyl-2-carbonyl)-amino]-quinoline-3-carboxic acid (dipyridin-2-yl-methyl)-amide, ethanesulfonate;
7-[(4'-trifluoromethyl-biphenyl-2-carbonyl)-amino]-quinoline-3-carboxylic acid (dipyridin-2-yl-methyl)-amide, bis-ethanesulfonate;
7-[(4'-trifluoromethyl-biphenyl-2-carbonyl)-amino]-quinoline-3-carboxylic acid (phenyl-pyridin-2-yl-methyl)-amide;
7-[(4'-trifluoromethyl-biphenyl-2-carbonyl)-amino]-quinoline-3-carboxylic acid (phenyl-pyridin-2-yl-methyl)-amide, ethanesulfonate;
(S)-7-[(4'-trifluoromethyl-biphenyl-2-carbonyl)-amino]-quinoline-3-carboxylic acid (phenyl-pyridin-2-yl-methyl)-amide;
(S)-7-[(4'-trifluoromethyl-biphenyl-2-carbonyl)-amino]-quinoline-3-carboxylic acid (phenyl-pyridin-2-yl-methyl)-amide, ethanesulfonate;
(S)-7-[(4'-trifluoromethyl-biphenyl-2-carbonyl)-amino]-quinoline-3-carboxylic acid (phenyl-pyridin-2-yl-methyl)-amide, bis-ethanesulfonate;
(R)-7-[(4'-trifluoromethyl-biphenyl-2-carbonyl)-amino]-quinoline-3-carboxylic acid (phenyl-pyridin-2-yl-methyl)-amide;
(R)-7-[(4'-trifluoromethyl-biphenyl-2-carbonyl)-amino]-quinoline-3-carboxylic acid (phenyl-pyridin-2-yl-methyl)-amide, ethanesulfonate;
7-[(4'-trifluoromethyl-biphenyl-2-carbonyl)-amino]-quinoline-3-carboxylic acid (phenyl-pyridin-2-yl-methyl)-amide, bis-ethanesulfonate;
7-[(4'-trifluoromethyl-biphenyl-2-carbonyl)-amino]-quinoline-3-carboxylic acid (1-carbamoyl-2-phenyl-ethyl)-amide;
7-[(4'-trifluoromethyl-biphenyl-2-carbonyl)-amino]-quinoline-3-carboxylic acid (carbamoyl-phenyl-methyl)-amide;
7-[(4'-trifluoromethyl-biphenyl-2-carbonyl)-amino]-quinoline-3-carboxylic acid propylamide;
7-[(4'-trifluoromethyl-biphenyl-2-carbonyl)-amino]-quinoline-3-carboxylic acid (2,2,2-trifluoro-ethyl)-amide;
7-[(4'-trifluoromethyl-biphenyl-2-carbonyl)-amino]-quinoline-3-carboxylic acid (1-methyl-1-phenyl-ethyl)-amide;
7-[(4'-trifluoromethyl-biphenyl-2-carbonyl)-amino]-quinoline-3-carboxylic acid cyclopentylamide;
7-[(4'-trifluoromethyl-biphenyl-2-carbonyl)-amino]-quinoline-3-carboxylic acid (1-phenyl-propyl)-amide;
(R)-7-[(4'-trifluoromethyl-biphenyl-2-carbonyl)-amino]-quinoline-3-carboxylic acid (1-phenyl-ethyl)-amide, ethanesulfonate;
7-[(4'-trifluoromethyl-biphenyl-2-carbonyl)-amino]-quinoline-3-carboxylic acid (1-phenyl-ethyl)-amide;

7-[(4'-trifluoromethyl-biphenyl-2-carbonyl)-amino]-quinoline-3-carboxylic acid (1-pyridin-2-yl-propyl)-amide;
(R)-7-[(4'-trifluoromethyl-biphenyl-2-carbonyl)-amino]-quinoline-3-carboxylic acid (1-pyridin-2-yl-propyl)-amide;
(R)-7-[(4'-trifluoromethyl-biphenyl-2-carbonyl)-amino]-quinoline-3-carboxylic acid (1-pyridin-2-yl-propyl)-amide, ethanesulfonate;
(S)-7-[(4'-trifluoromethyl-biphenyl-2-carbonyl)-amino]-quinoline-3-carboxylic acid (1-pyridin-2-yl-propyl)-amide;
(S)-7-[(4'-trifluoromethyl-biphenyl-2-carbonyl)-amino]-quinoline-3-carboxylic acid (1-pyridin-2-yl-propyl)-amide ethanesulfonate;
7-[(4'-trifluoromethyl-biphenyl-2-carbonyl)-amino]-quinoline-3-carboxylic acid (1-pyridin-2-yl-propyl)-amide, ethanesulfonate;
7-[(4'-trifluoromethyl-biphenyl-2-carbonyl)-amino]-quinoline-3-carboxylic acid (pyridin-2-ylmethyl)-amide, ethanesulfonate;
7-[(4'-trifluoromethyl-biphenyl-2-carbonyl)-amino]-quinoline-3-carboxylic acid (2-pyridin-2-yl-ethyl)-amide, ethanesulfonate;
7-[(4'-trifluoromethyl-biphenyl-2-carbonyl)-amino]-quinoline-3-carboxylic acid ethylamide, ethanesulfonate;
7-[(4'-trifluoromethyl-biphenyl-2-carbonyl)-amino]-quinoline-3-carboxylic acid butylamide, ethanesulfonate;
7-[(4'-trifluoromethyl-biphenyl-2-carbonyl)-amino]-quinoline-3-carboxylic acid (thiophen-2-ylmethyl)-amide, ethanesulfonate;
7-[(4'-trifluoromethyl-biphenyl-2-carbonyl)-amino]-quinoline-3-carboxylic acid (1-methyl-1-pyridin-2-yl-ethyl)-amide;
(S)-7-[(4'-trifluoromethyl-biphenyl-2-carbonyl)-amino]-quinoline-3-carboxylic acid (1-pyridin-2-yl-ethyl)-amide;
(R)-7-[(4'-trifluoromethyl-biphenyl-2-carbonyl)-amino]-quinoline-3-carboxylic acid (1-pyridin-2-yl-ethyl)-amide ethanesulfonate;
7-[(4'-trifluoromethyl-biphenyl-2-carbonyl)-amino]-quinoline-3-carboxylic acid (1-pyridin-2-yl-ethyl)-amide;
7-[(4'-trifluoromethyl-biphenyl-2-carbonyl)-amino]-quinoline-3-carboxylic acid (1-pyridin-2-yl-ethyl)-amide ethanesulfonate;
7-[(4'-trifluoromethyl-biphenyl-2-carbonyl)-amino]-quinoline-3-carboxylic acid amide;
7-[(4'-trifluoromethyl-biphenyl-2-carbonyl)-amino]-quinoline-3-carboxylic acid benzylamide;
7-[(4'-trifluoromethyl-biphenyl-2-carbonyl)-amino]-quinoline-3-carboxylic acid 4-methoxy-benzylamide;
7-[(4'-trifluoromethyl-biphenyl-2-carbonyl)-amino]-quinoline-3-carboxylic acid 4-chloro-benzylamide;
7-[(4'-trifluoromethyl-biphenyl-2-carbonyl)-amino]-quinoline-3-carboxylic acid 4-methyl-benzylamide;
7-[(4'-trifluoromethyl-biphenyl-2-carbonyl)-amino]-quinoline-3-carboxylic acid cyclopropylmethyl-amide;
7-[(4'-trifluoromethyl-biphenyl-2-carbonyl)-amino]-quinoline-3-carboxylic acid 4-fluoro-benzylamide;
7-[(4'-trifluoromethyl-biphenyl-2-carbonyl)-amino]-quinoline-3-carboxylic acid isopropyl-amide;
7-[(4'-trifluoromethyl-biphenyl-2-carbonyl)-amino]-quinoline-3-carboxylic acid benzhydryl-amide;
7-[(4'-trifluoromethyl-biphenyl-2-carbonyl)-amino]-quinoline-3-carboxylic acid cyclopropylamide;
7-[(4'-trifluoromethyl-biphenyl-2-carbonyl)-amino]-quinoline-3-carboxylic acid [1-(4-fluoro-phenyl)-ethyl]-amide;
7-[(4'-trifluoromethyl-biphenyl-2-carbonyl)-amino]-quinoline-3-carboxylic acid 3-methyl-benzylamide;
7-[(4'-trifluoromethyl-biphenyl-2-carbonyl)-amino]-quinoline-3-carboxylic acid 3-methoxy-benzylamide;
7-[(4'-trifluoromethyl-biphenyl-2-carbonyl)-amino]-quinoline-3-carboxylic acid 3-chloro-benzylamide;
7-[(4'-trifluoromethyl-biphenyl-2-carbonyl)-amino]-quinoline-3-carboxylic acid 2-fluoro-benzylamide;
7-[(4'-trifluoromethyl-biphenyl-2-carbonyl)-amino]-quinoline-3-carboxylic acid 3-fluoro-benzylamide;
7-[(4'-trifluoromethyl-biphenyl-2-carbonyl)-amino]-quinoline-3-carboxylic acid 2-methyl-benzylamide;
7-[(4'-trifluoromethyl-biphenyl-2-carbonyl)-amino]-quinoline-3-carboxylic acid 2-methoxy-benzylamide;
7-[(4'-trifluoromethyl-biphenyl-2-carbonyl)-amino]-quinoline-3-carboxylic acid 2-chloro-benzylamide;
4'-trifluoromethyl-biphenyl-2-carboxylic acid [3-(pyrrolidin-1-carbonyl)-quinolin-7-yl]-amide;
4'-trifluoromethyl-biphenyl-2-carboxylic acid [3-(morpholine-4-carbonyl)-quinolin-7-yl]-amide;
7-[(4'-trifluoromethyl-biphenyl-2-carbonyl)-amino]-quinoline-3-carboxylic acid diethylamide;
4'-trifluoromethyl-biphenyl-2-carboxylic acid [3-(piperidine-1-carbonyl)-quinolin-7-yl]-amide; and the pharmaceutically acceptable salts and prodrugs thereof, and salts of the prodrugs.

In addition, a neurotensin receptor ligand can be used in combination with one or more additional compounds that are neurotensin receptor ligands such as those set forth above.

Some abbreviations used in this application are defined below:

| | |
|---|---|
| GTP | Guanosine 5'-triphosphate |
| GDP | Guanosine 5'-diphosphate |
| DTT | Dithiothreitol |
| PEI | Polyethylene imine |
| FLIPR | Flouresence imaging plate reader |
| DMSO | Dimethylsulfoxide |
| HEPES | (N-[2-Hydroxyethyl]piperazine-N'-[2-ethanesulfonic acid]) |
| NT | Neurotensin |
| BSA | Bovine serum albumin |
| PBS | Phosphate buffered saline |
| EDTA | Ethylenediaminetetraacetic acid |
| EGTA | Ethylene glycol-bis(β-aminoethyl ether) N,N,N',N'-tetraacetic acid |

All documents cited herein are hereby incorporated by reference.

The examples presented below are intended to illustrate particular embodiments of the invention, and are not intended to limit the scope of the specification, including the claims, in any manner.

EXAMPLES

Saturation Binding: GTP$_\gamma$[$^{35}$S] Binding

Agonist-stimulated GTP$_\gamma$[$^{35}$S] binding is a reliable method for the determination of agonist efficacy and potency at G-protein-coupled receptors (GPCRs). GDP binds preferentially over GTP at unactivated heterotrimeric G protein alpha subunits. When an agonist activates a GPCR, the GDP is displaced by GTP (or GTP analogs) causing dissociation of the alpha subunit from the beta and gamma subunits of the heterotrimeric G protein. To measure agonist efficacy and potency $CTP_\gamma[^{35}S]$ is used instead of GTP.

| Well | − | + | STOCK $[GTP\gamma[^{35}S]]$ | FINAL $[GTP\gamma[^{35}S]]$ |
|---|---|---|---|---|
| A | 1, 2 | 3, 4 | 1 nM | 0.05 nM |
| B | 1, 2 | 3, 4 | 2 nM | 0.1 nM |
| C | 1, 2 | 3, 4 | 5 nM | 0.25 nM |
| D | 1, 2 | 3, 4 | 10 nM | 0.5 nM |
| E | 1, 2 | 3, 4 | 15 nM | 0.75 nM |
| F | 1, 2 | 3, 4 | 20 nM | 1 nM |
| G | 1, 2 | 3, 4 | 100 nM | 5 nM |
| H | 1, 2 | 3, 4 | 200 nM | 10 nM |

Specific Activity of $CTP_\gamma[^{35}S]$ is approximately 1250 Ci/mmole. The useful life of $CTP_\gamma[^{35}S]$ is about one month. Radioactivity calculators that are well know to those skilled in the art can be used to determine the actual concentration of stock $CTP_\gamma[^5S]$.

To each well add in order:

20 μl binding buffer to "−" wells

20 μl of neurotensin in binding buffer (1 μM final) to "+" wells

10 μl appropriate concentration of $CTP_\gamma[^{35}S]$ in binding buffer

170 μl membranes from cells expressing neurotensin receptors diluted to 20 μg/170 μl in binding buffer.

Binding buffer:

50 mM Hepes/5 mM $MgCl_2$, pH 7.4

150 mM NaCl

2 μM GDP 1 mM dithiothreitol (DTT)

Protease inhibitors
  100 μg/ml bacitracin
  100 μg/ml benzamidine
  5 μg/ml aprotinin
  5 μg/ml leupeptin The protease inhibitors can be obtained from Sigma, St. Louis, Mo.

Wash buffer:

50 mM Hepes/10 mM $MgCl_2$, pH 7.4, ice cold

Procedure:

1. Set up assay in a 96 well filtering system (Unifilter® GF/C™, Packard Instrument Company, Meriden, Conn.).
2. Incubate 60–90 minutes shaking at room temperature.
3. Using a cell Harvester, aspirate samples into processing head. Use a pre-soaked (water is fine) filter. (Do not use polyethylene imine (PEI))
4. Wash four times with cold wash buffer.
5. Dry plate, add 25 μl of scintillation fluid to each well.
6. Count samples.

Data Analysis:

Analyze data as you would for a radioligand binding saturation curve. Subtract the mean of the "minus" wells from the mean of the "plus" wells. Then convert to pmoles/mg protein bound and perform non-linear regression to determine the $K_d$ for $CTP_\gamma[^{35}S]$ binding.

$Ca^{++}$ Mobilization Using the FLIPR Assay

Another measure of agonist efficacy and potency is the stimulation of intracellular calcium release. Receptors coupled to the heterotrimeric G protein Gq leads to stimulation of phospholipase C. Activation of Phospholipase C leads to the production of diacylgylerol and 1,4,5-inositol-trisphosphate ($IP_3$). $IP_3$ then binds to $IP_3$ receptors stimulating release of intracellular $Ca^{++}$. Stimulation of $Ca^{++}$ release can be measured using fluorescent dyes that bind $Ca^{++}$ such as Fluo-4AM and Fura-2AM (Molecular Probes, Inc., Eugene, Oreg.). The following is a protocol for measuring intracellular $Ca^{++}$ release mediated by neurotensin agonists. The measurement of $Ca^{++}$ released upon GPCR activation is known to those skilled in the art and other methods can also be used.

All solution components are listed below.

1. Prepare hepes saline and probenecid solutions fresh for each assay. 1 L of assay buffer is sufficient for a small-scale experiment.
2. Prepare 11 ml dye solution per 96 well cell plate. Aliquot 100 μl per well; incubate at 37° C., $CO_2$ incubator, 1 hour.
3. Prepare plate containing compound to be tested, diluting compound to be tested in assay buffer (prepare assay buffer just before use). Allow 100 μl excess compound to be tested volume per well. For example, if 50 μl compound to be tested will be added to 100 μl cells, then add 150 μl 3× concentrated compound per well.
4. Empty media from cell plate and wash with assay buffer on scatron plate washer (if doing large amounts of plates). For smaller amount of plates, can aspirate carefully. Equilibrate cells 10 minutes in assay buffer.
5. Load cell plate and drug plate into FLIPR; run experiment.

Hepes saline—1 L 29 ml 5 M NaCl (145 mM final)

5 ml 2M Glucose (10 mM final)

1.65 ml 3M KCl (5 mM final)

1 ml 1M $MgSO_4$ (1 mM final)

10 ml 1M Hepes (10 mM final)

2 ml 1M $CaCl_2$ (2 mM final)

Probenecid Solution—12.5 ml 925 mg probenecid (2.5 mM final)

1.25 ml 5 N NaOH 11.25 ml Hepes saline

Dye solution (11 ml)

1. Combine 11 ml serum-free medium and 110 μl probenecid solution.
2. In a separate tube, add 22 μl dimethylsulfoxide (DMSO) to one vial fluo-4 AM; resuspend by pipetting up and down. Add 22 μl 20% pluronics to this vial. Mix by pipetting—pluronics is very viscous. NOTE: Two fluo-4 vials can be used, and will result in a stronger signal. In this case, double DMSO/pluronics volumes.
3. Add fluo-3/pluronics suspension to serum-free medium; mix well by inversion.

Assay Buffer (1% probenecid solution in hepes saline)

10 ml probenecid solution

1 L hepes saline

Saturation Binding: [$^{125}$I]Neurotensin (NT) at Neurotensin Receptors

| Well | − | + | Final [[$^{125}$I]NT] |
|---|---|---|---|
| A | 1, 2 | 3, 4 | 0.02 nM |
| B | 1, 2 | 3, 4 | 0.05 nM |
| C | 1, 2 | 3, 4 | 0.75 nM |
| D | 1, 2 | 3, 4 | 0.10 nM |
| E | 1, 2 | 3, 4 | 0.25 nM |
| F | 1, 2 | 3, 4 | 0.50 nM |
| G | 1, 2 | 3, 4 | 0.75 nM |
| H | 1, 2 | 3, 4 | 1.00 nM |

Total volume in each well is 200 µl.

Specific activity of [$^{125}$I]NT is 2200 Ci/mmole. Radioactivity calculators that are well known in the art can be used to calculate the specific activities of the stock solutions.

To each well add in order:
20 µl buffer to "−" wells
20 µl 10 µM NT to "+" wells
10 µl appropriate concentration of [$^{125}$I]NT
170 µl membranes diluted to 10 µg/170 µl
Binding buffer:
50 mM Hepes/10 mM MgCl$_2$, pH 7.4
0.2% BSA (fraction V)
Protease inhibitors
  100 µg/ml bacitracin
  100 µg/ml benzamidine
  5 µg/ml aprotinin
  5 µg/ml leupeptin
Wash buffer:
50 mM Hepes/10 mM MgCl$_2$, pH 7.4, ice cold.
Procedure:
1. Set up assay in a 96 well filtering system (Unifilter® GF/C™, Packard Instrument Company, Meriden, Conn.).
2. Incubate 90–120 minutes shaking at room temperature
3. Using a cell Harvester, aspirate samples into processing head. Use a filter pre-soaked is 0.3% PEI.
4. Wash four times with cold wash buffer.
5. Dry plate, add 25 µl scintillation fluid to each well.
6. Count samples.
Data Analysis Subtract the mean of the "plus" wells from the mean of the "minus" wells. Then convert to fmoles/mg protein bound and perform non-linear regression to determine the K$_d$ for [$^{125}$I]NT binding.

Note: This procedure can be modified to use tritiated neurotensin.

Competition Binding: [$^{125}$I]NT at Neurotensin Receptors

Up to seven compounds can be tested in 7 point competition curves in a 96 well format. The first six rows for each compound will be used for testing 6 compounds at 6 concentrations in duplicate. An example for a single compound is outlined below. The next compound would be in rows A–F, columns 3 and 4. A seventh compound can be placed in row G1–12 (−9 to −4).

A1,2 −9
B1,2 −8
C1,2 −7
D1,2 −6
E1,2 −5
F1,2 −4

Wells H1,2 are for total counts per minute (cpm) bound.
Wells H3,4 are for 1 µM NT to determine non-specific binding.
Filter blanks (just buffer, no membranes) are in H5,6.

Samples are made in the following stock concentrations: $10^{-3}$, $10^{-4}$, $10^{-5}$, $10^{-6}$, $10^{-7}$, $10^{-8}$ M. The final concentrations will be one order of magnitude less ($10^{-4}$ to $10^{-9}$). Stock concentration of compounds are usually 25 mM so a 25:1 dilution is required. Make up 6 tubes labeled −4 to −9. Put 100 µl of binding buffer in each tube. Add 4 µl of 25 mM stock to the tube labeled −4. Vortex and take 11 µl of the −4 sample and add to the −5 tube. Repeat until all the dilutions are made.

To each well add in order:
20 µl buffer to "total" wells (H1, 2).
20 µl 10 µM NT to wells H3, 4.
170 µl buffer to wells H5, 6.
20 µl of each concentration of compound to the appropriate wells.
10 µl of 5 nM [$^{125}$I]NT to all wells.
170 µl membranes diluted to 10 µg/170 µl.
Procedure:
1. Set up assay in a 96 well filtering system (Unifilter® GF/C™, Packard Instrument Company, Meriden, Conn.).
2. Incubate 90–120 minutes shaking at room temperature.
3. Using a cell Harvester, aspirate samples into processing head. Use a pre-soaked (0.3% PEI) filter.
4. Wash four times with cold wash buffer.
5. Dry plate, add 25 µl of scintillation fluid to each well.
6. Count samples.
Binding buffer:
50 mM Hepes/10 mM MgCl$_2$, pH 7.4 (Made from 10× stock)
0.2% BSA (fraction V)
Protease inhibitors (Made up as 100× stock).
  100 µg/ml bacitracin
  100 µg/ml benzamidine
  5 µg/ml aprotinin
  5 µg/ml leupeptin
Wash buffer:
50 mM Hepes/10 mM MgCl$_2$, pH 7.4, ice cold (Made from 10× stock).

Agonist-Mediated CTP$_\gamma$[$^{35}$S]Binding Assay

Up to seven compounds can be tested in 7 point competition curves in a 96 well format. The first six rows for each compound will be used for testing 6 compounds at 6 concentrations in duplicate. An example for a single compound is outlined below. The next compound would be in rows A–F, columns 3 and 4. A seventh compound can be placed in row G1–12 (−9 to −4).

A1,2 −9
B1,2 −8
C1,2 −7
D1,2 −6
E1,2 −5
F1,2 −4

Wells H1–4 are for basal CTP$_\gamma$[$^{35}$S] bound.
Wells H5,6 are for cold 10 µM CTP$_\gamma$S to determine non-specific binding.
Filter blanks (just buffer, no membranes) are in H7,8.

Samples are made in the following stock concentrations: $10^{-3}$, $10^{-4}$, $10^{-5}$, $10^{-6}$, $10^{-7}$, $10^{-8}$ M. The final concentrations will be one order of magnitude less ($10^{-4}$ to $10^{-9}$). Stock concentration of compounds are usually 25 mM so a 25:1 dilution is required. Make up 6 tubes labeled −4 to −9. Put 100 µl of binding buffer in each tube. Add 4 µl of 25 mM stock to the tube labeled −4. Vortex and take 11 µl of the −4 sample and add to the −5 tube. Repeat until all the dilutions are made. The first sample is always native neurotensin.

To each well add in order:

20 µl binding buffer to wells H1–4.

20 µl of each concentration of compound to the appropriate wells.

20 µl of 100 µM $CTP_\gamma S$ to wells H5,6.

10 µl appropriate concentration of $CTP_\gamma[^{35}S]$

170 µl membranes diluted to 20 µg/170 µl in binding buffer.

$CTP_\gamma S$ binding buffer:
(Make fresh)
50 mM Hepes/5 mM $MgCl_2$, pH 7.4
150 mM NaCl (3M)
2 µM GDP (10 mM)
1 mM DTT (1 M)
Protease inhibitors
   100 µg/ml bacitracin
   100 µg/ml benzamidine
   5 µg/ml aprotinin
   5 µg/ml leupeptin
Wash buffer:
50 mM Hepes/10 mM $MgCl_2$, pH 7.4, ice cold
Procedure:

1. Set up assay in a 96 well filtering system (Unifilter® GF/C™, Packard Instrument Company, Meriden, Conn.).
2. Incubate 60 minutes shaking at room temperature.
3. Using a cell Harvester, aspirate samples into processing head. Use a pre-soaked (water is fine) filter. Do not use PEI.
4. Wash four times with cold wash buffer.
5. Dry plate, add 25 µl scintillation fluid to each well.
1. 6. Count samples.

Data Analysis:

Analyze data as you would for a dose response curve. Convert to pmoles/mg bound.

Membrane Preparations from Cells

2. Harvest cells. For adherent cells (usually prepare 10 150 mm plates) use PBS/EDTA to remove the cells. Spin down at 1000×g for 10 minutes at 4° C. Remove supernatant and resuspend in 10 ml homogenization buffer. Let sit on ice for 10 minutes. It is noted that the cells such as HEK293 or CHO cells expressing recombinant neurotensin receptors can be used. In addition, native neurotensin receptor such as HT29 or SW cells can be used.
3. Homogenize with 20 strokes of a tight-fitting glass/glass dounce homogenizer.
4. Spin out nuclei and unlysed cells by centrifuging samples at 1000×g for 10 minutes at 4° C.
5. Transfer supernatant to new tube.
6. Do two centrifugations at 25,000×g for 20 minutes in a Sorvall SS34 (or comparable) at 4° C.
7. Resuspend in an appropriate volume of homogenization buffer that will yield a protein concentration 1–5 mg/ml. Make 250 µl aliquots of each sample plus one 10 µl aliquot for protein determination. For the protein assay dilute 1:5 and measure.

10× Homogenization buffer
10 mM EDTA
10 mM EGTA
10 mM Na bicarbonate pH 7.4
100× Protease inhibitors
10 mg/ml benzamidine
10 mg/ml bacitracin
0.5 mg/ml leupeptin
0.5 mg/ml aprotinin

What is claimed is:

1. A method of treating obesity, the method comprising the step of administering to an obese patient or a patient at risk of becoming obese a therapeutically effective amount of a compound that is a selective neurotensin-1 receptor agonist, wherein said agonist is not neurotensin.

* * * * *